United States Patent
Suga

(10) Patent No.: US 10,234,460 B2
(45) Date of Patent: Mar. 19, 2019

(54) MACROCYCLIC PEPTIDE, METHOD FOR PRODUCING SAME, AND SCREENING METHOD USING MACROCYCLIC PEPTIDE LIBRARY

(71) Applicant: The University of Tokyo, Tokyo (JP)

(72) Inventor: Hiroaki Suga, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 14/914,634

(22) PCT Filed: Aug. 26, 2014

(86) PCT No.: PCT/JP2014/072338
§ 371 (c)(1),
(2) Date: Mar. 8, 2016

(87) PCT Pub. No.: WO2015/030014
PCT Pub. Date: Mar. 5, 2015

(65) Prior Publication Data
US 2016/0209421 A1 Jul. 21, 2016

(30) Foreign Application Priority Data
Aug. 26, 2013 (JP) ................ 2013-174906

(51) Int. Cl.
| | | |
|---|---|---|
| C07K 7/64 | (2006.01) | |
| G01N 33/68 | (2006.01) | |
| C07K 7/06 | (2006.01) | |
| C07K 7/08 | (2006.01) | |
| C12P 21/02 | (2006.01) | |

(52) U.S. Cl.
CPC ........... *G01N 33/6845* (2013.01); *C07K 7/06* (2013.01); *C07K 7/08* (2013.01); *C07K 7/64* (2013.01); *C12P 21/02* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 2006/0004185 A1 | 1/2006 | Leese et al. | |
| 2010/0022448 A1* | 1/2010 | New ................ | C07K 7/64 514/1.1 |
| 2013/0178394 A1 | 7/2013 | Suga et al. | |
| 2013/0203654 A1 | 8/2013 | Sekimizu et al. | |
| 2014/0018257 A1 | 7/2014 | Suga et al. | |

FOREIGN PATENT DOCUMENTS

| | | |
|---|---|---|
| JP | 2008-505858 A | 2/2008 |
| JP | 2010-504313 A | 2/2010 |
| JP | 2012-006917 A | 1/2012 |
| JP | 2012-058092 A | 3/2012 |
| WO | 2003034071 A1 | 4/2003 |
| WO | 2012074130 A1 | 6/2012 |

OTHER PUBLICATIONS

Written Opinion received in PCT/JP2014/072338, dated Nov. 18, 2014.
International Search Report received in PCT/JP2014/072338, dated Nov. 18, 2014.
Murakami, et al., "A Versatile tRNA Aminoacylation Catalyst Based on RNA", Jul. 2003, pp. 655-662, No. 10, Publisher: Chemistry & Biology.
White, et al., "On-Resin N-Methylation of Cyclic Peptides for Discovery of Orally Bioavailable Scaffolds", Sep. 25, 2011, pp. 810-817, vol. 7, No. 11, Publisher: Nature Chemical Biology.
Reza, et al., "Development and application of dynamic virtual bicyclic peptides as a prospective therapeutic scaffold", Mar. 25, 2013, Publisher: University of Tokyo.
Kawakami, et al., "Diverse backbone-cyclized peptides via codon reprogramming", Oct. 25, 2009, pp. 888-890, vol. 5, Publisher: Nature Chemical Biology.
Morimoto, et al., "Discovery of Macrocyclic Peptides Armed with a MechanismBased Warhead: IsoformSelective Inhibition of Human Deacetylase SIRT2*", Feb. 28, 2012, pp. 3423-3427, vol. 51, No. 14, Publisher: Angewandte Chemie International Edition/.
Yamagishi, et al., "Natural Product-Like Macrocyclic N-Methyl-Peptide Inhibitors against a Ubiquitin Ligase Uncovered from a Ribosome-Expressed De Novo Library", Dec. 22, 2011, pp. 1562-1570, vol. 18, No. 12, Publisher: Chem Biol.
Cheng, et al., "Molecular Dynamics Investigation of Nanotube Diameter and Wall Thickness of Cyclic Hexa-, Octa-, Deca- and Dodeca-Peptide", Jun. 1, 2013, pp. 1335-1337, vol. 10, No. 6, Publisher: Journal of Computational and Theoretical Nanoscience.
EPO Communication pursuant to Article 94(3) EPC received in EP 14839993.4 dated Nov. 23, 2018.
Illesinghe, et al., "Metathesis assisted synthesis of cyclic peptides", Dec. 3, 2008, pp. 295-297, vol. 3, Publisher: Chem. Commun.
Jiang, et al., "Design and synthesis of redox stable analogues of sunflower trypsin inhibitors (SFTI-1) on solid support, potent inhibitors of matriptase", Jan. 4, 2007, pp. 9-12, vol. 9, No. 1, Publisher: Org Lett.

* cited by examiner

Primary Examiner — Christopher M Gross
(74) Attorney, Agent, or Firm — Suzannah K. Sundby, Esq.; Canady + Lortz LLP

(57) ABSTRACT

An object of the present invention is to provide a peptide excellent in resistance against metabolism, having a stable structure in vivo, and capable of penetrating a cell membrane and reaching in cells. The present invention provides a macrocyclic peptide having a macrocyclic structure comprised of four or more amino acids. At least two amino acids not adjacent to each other have a hydrophobic side chain and the hydrophobic side chains interact with each other inside the ring of the macrocyclic peptide in a hydrophilic environment.

10 Claims, 13 Drawing Sheets
Specification includes a Sequence Listing.

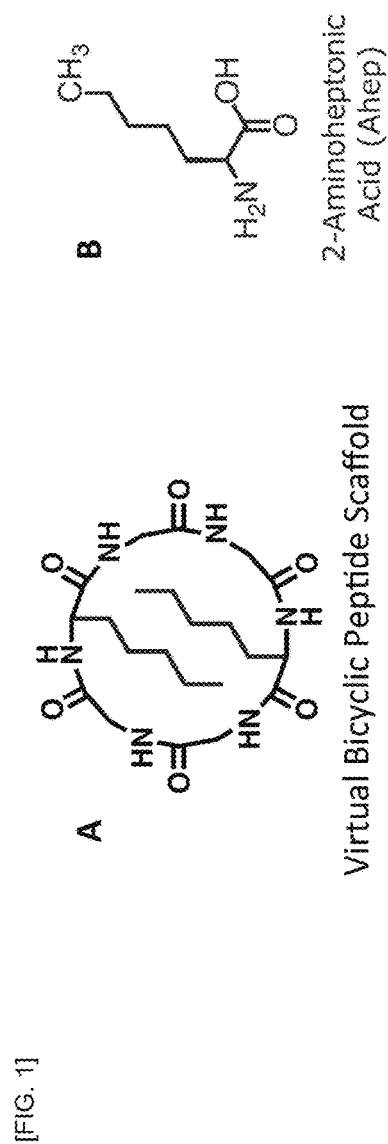
[FIG. 1]

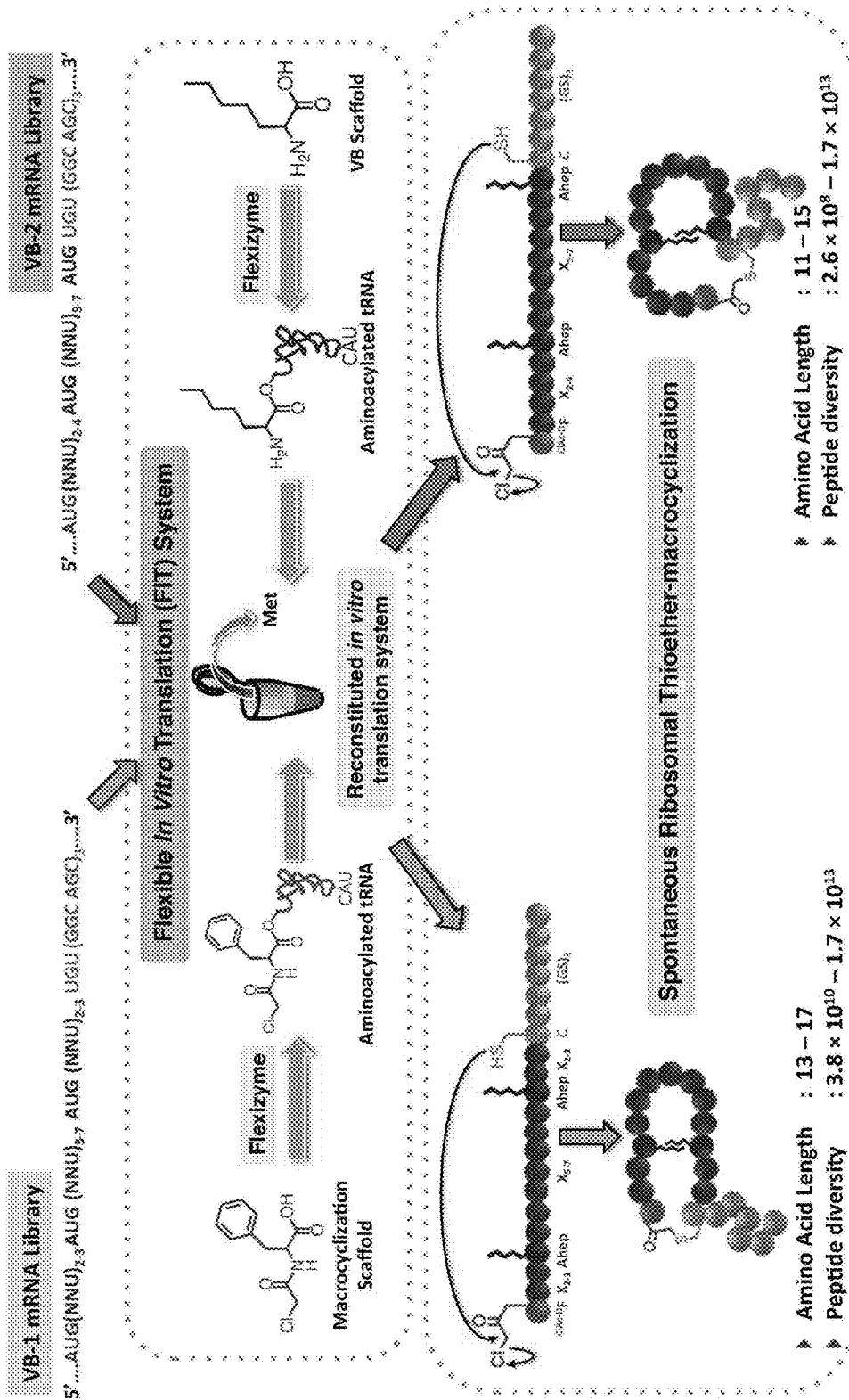
[FIG. 2]

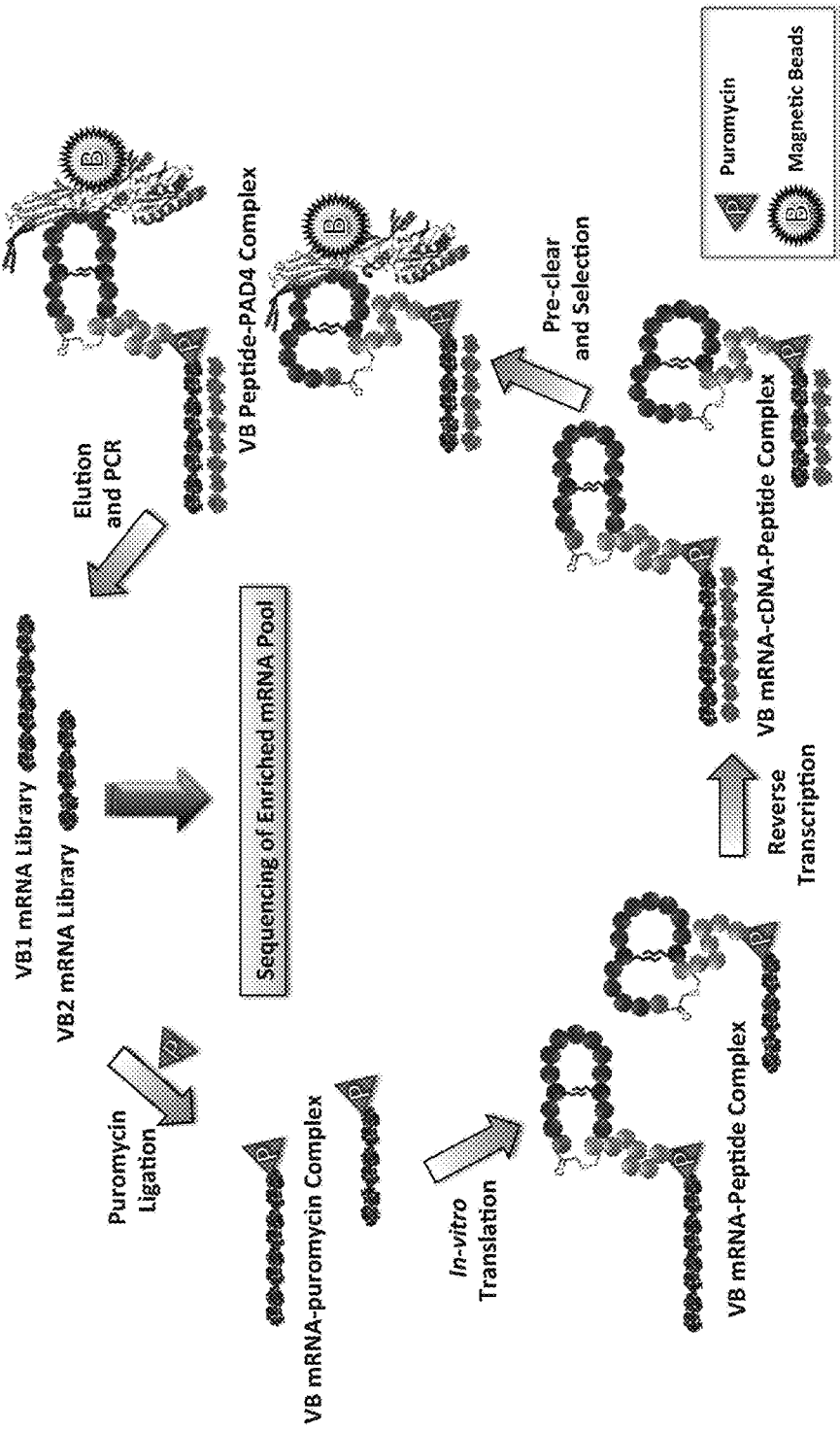
[FIG. 3]

[FIG. 4]
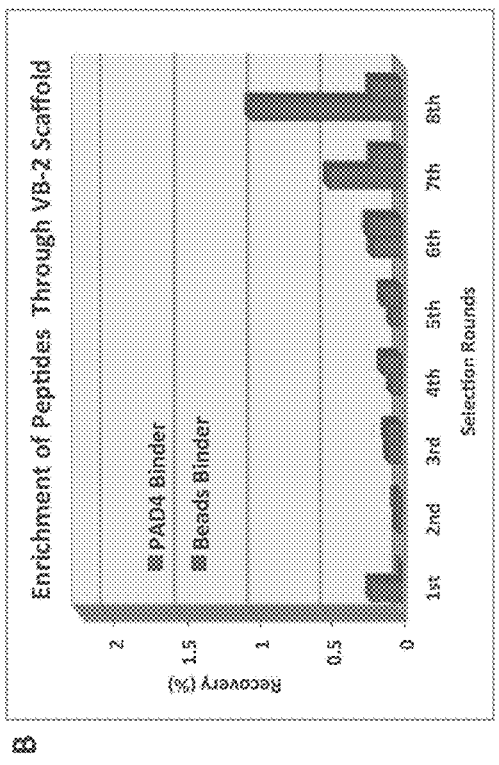
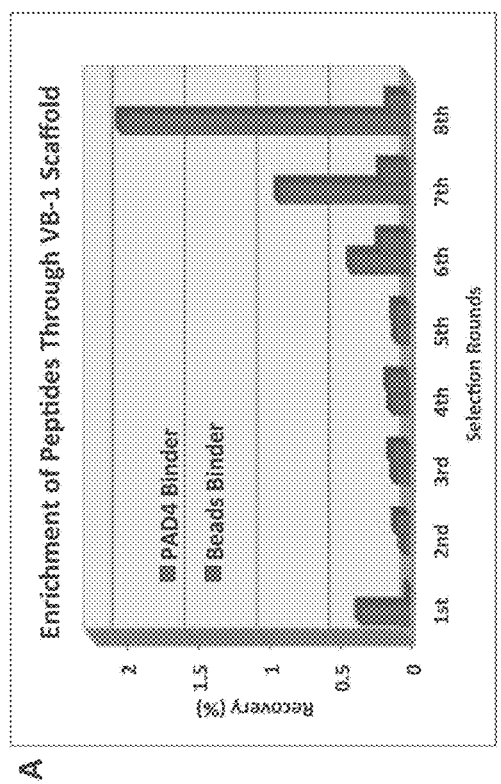

[FIG. 5]

| Name | Peptide Sequences | Scaffold | $K_D$ (nM) | $K_a$ ($M^{-1}s^{-1}$) | $K_d$ ($s^{-1}$) |
|---|---|---|---|---|---|
| VBIC12 | Ac-D<sub>F</sub> N A Ahep Y P Y R P P Ahep T S C G (with S bridge and C-G bridge) | Virtual Bicyclic | 54.98 | $1.21×10^5$ | $6.64×10^{-3}$ |
| VBIC20 | Ac-D<sub>F</sub> D A Ahep Y P F R P P Ahep A H C G (with S bridge and C-G bridge) | Virtual Bicyclic | 38.71 | $9.21×10^4$ | $3.56×10^{-3}$ |

[FIG. 6]
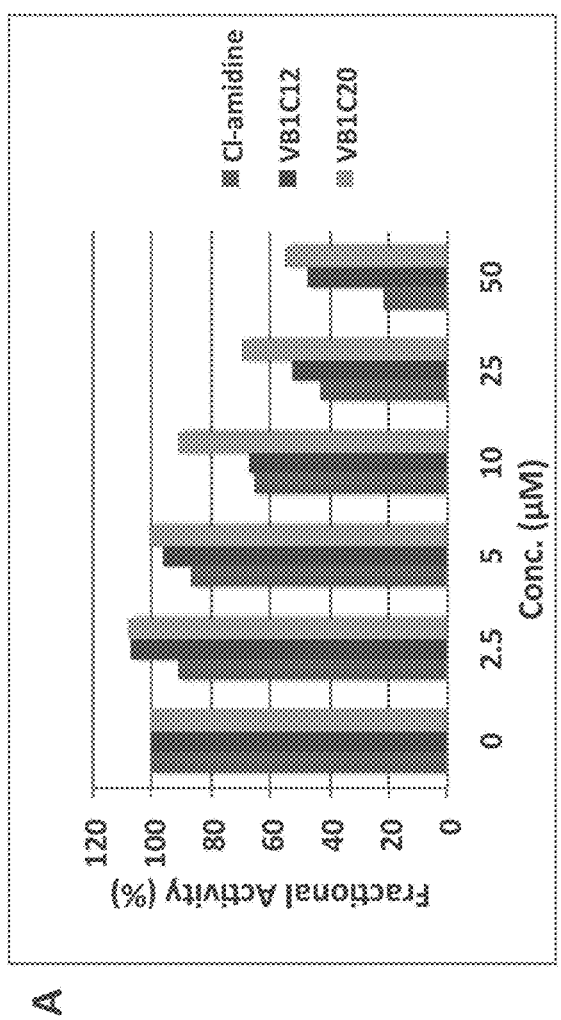
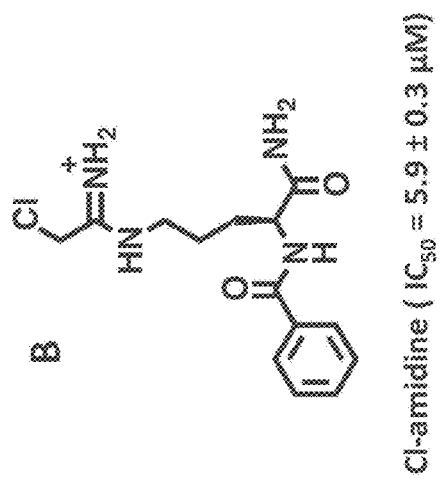

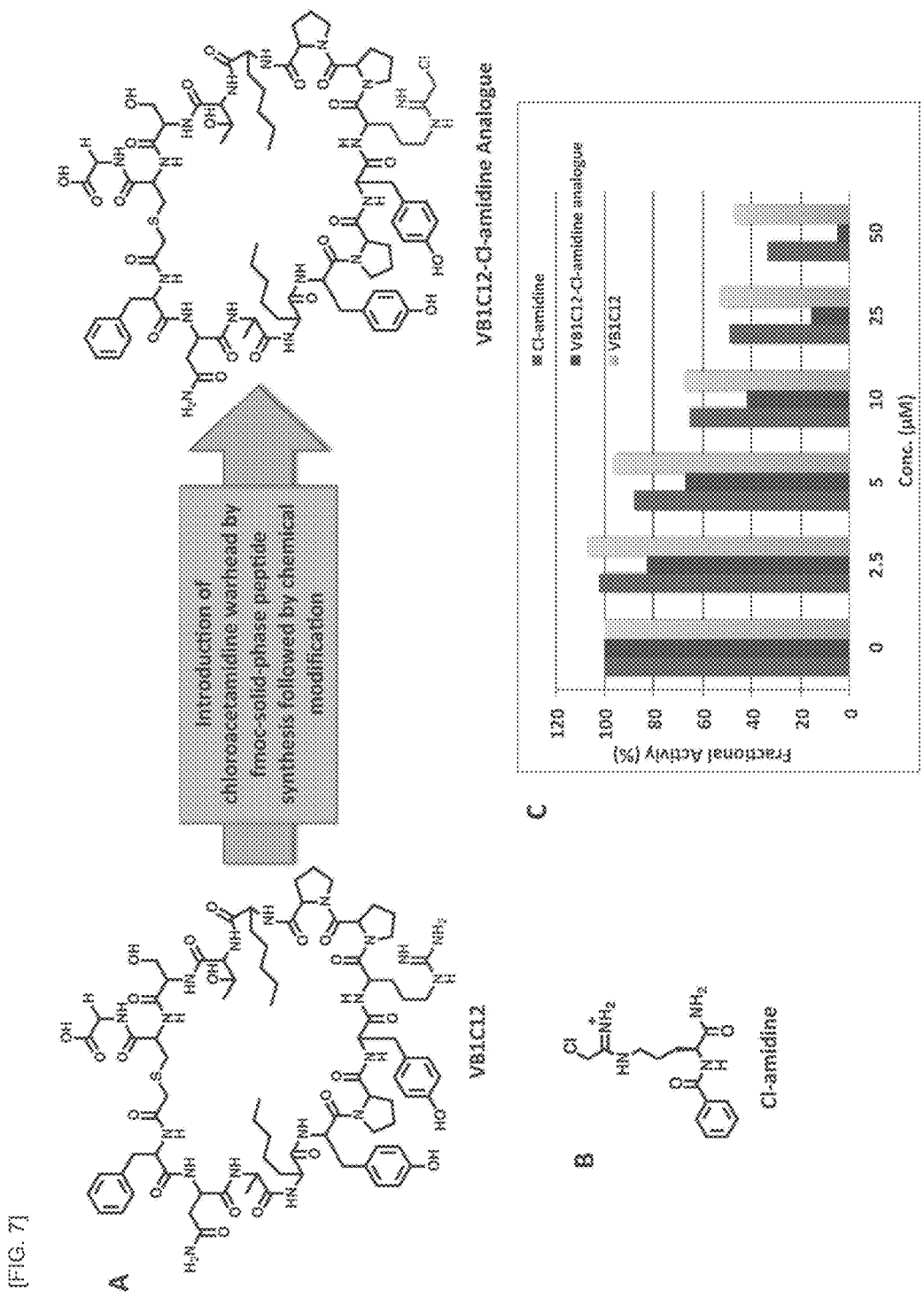
[FIG. 7]

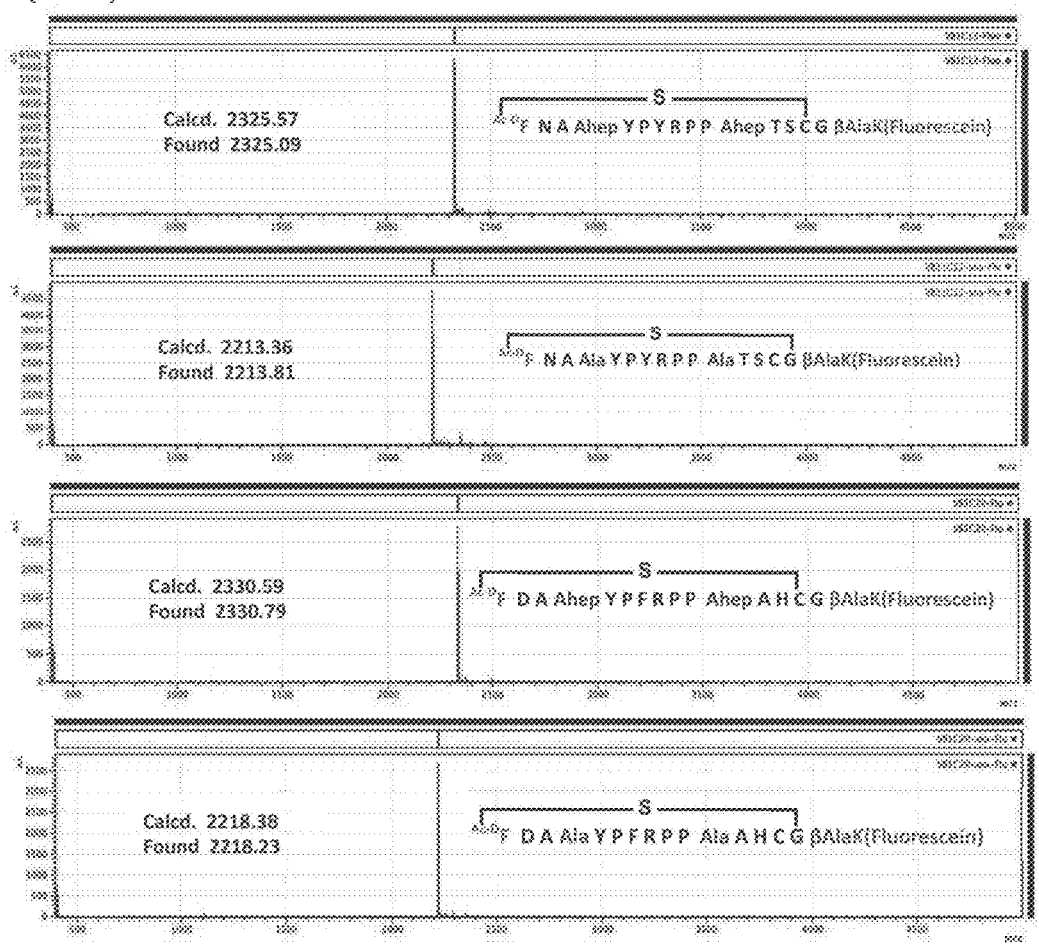
[FIG. 8]

[FIG. 9]

| | DIC | Fluorescein | DRAQ7 | Merged |
|---|---|---|---|---|
| DMSO (0.5%) | | | | |
| VB1C12-Flu (1µM) | | | | |
| VB1C12-Flu (5µM) | | | | |
| VB1C12-Flu (10µM) | | | | |
| VB1C12-ana-Flu (1µM) | | | | |
| VB1C12-ana-Flu (5µM) | | | | |
| VB1C12-ana-Flu (10µM) | | | | |

[FIG. 10]

| | DIC | Fluorescein | DRAQ7 | Merged |
|---|---|---|---|---|
| DMSO (0.5%) | | | | |
| VB1C20-Flu (1μM) | | | | |
| VB1C20-Flu (5μM) | | | | |
| VB1C20-Flu (10μM) | | | | |
| VB1C20-ana-Flu (1μM) | | | | |
| VB1C20-ana-Flu (5μM) | | | | |
| VB1C20-ana-Flu (10μM) | | | | |

[FIG. 11]
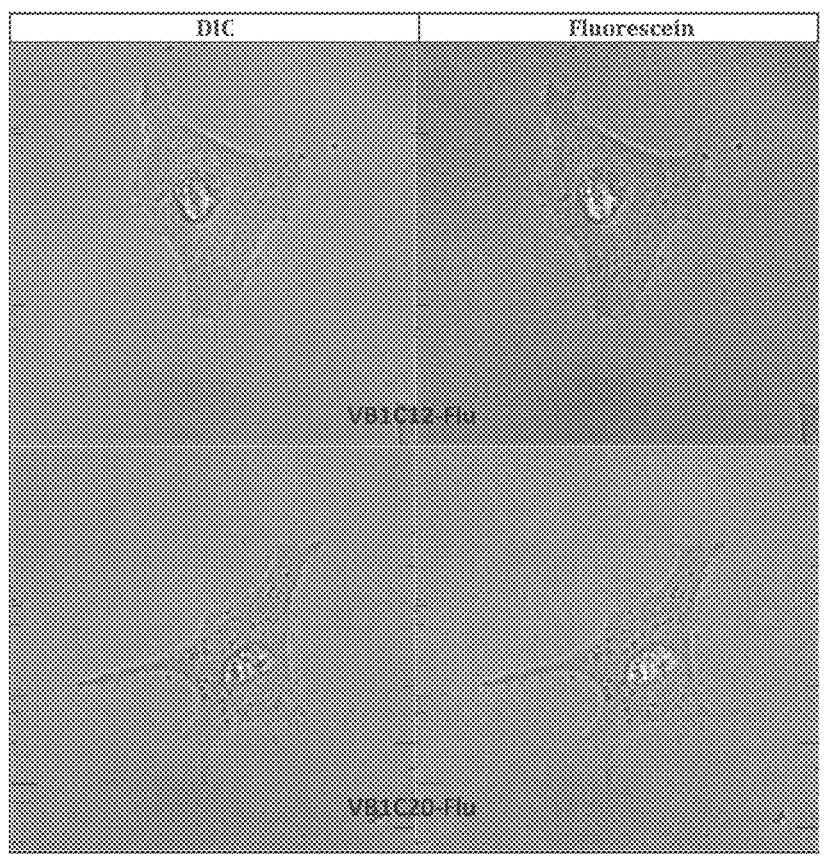

[FIG. 12]
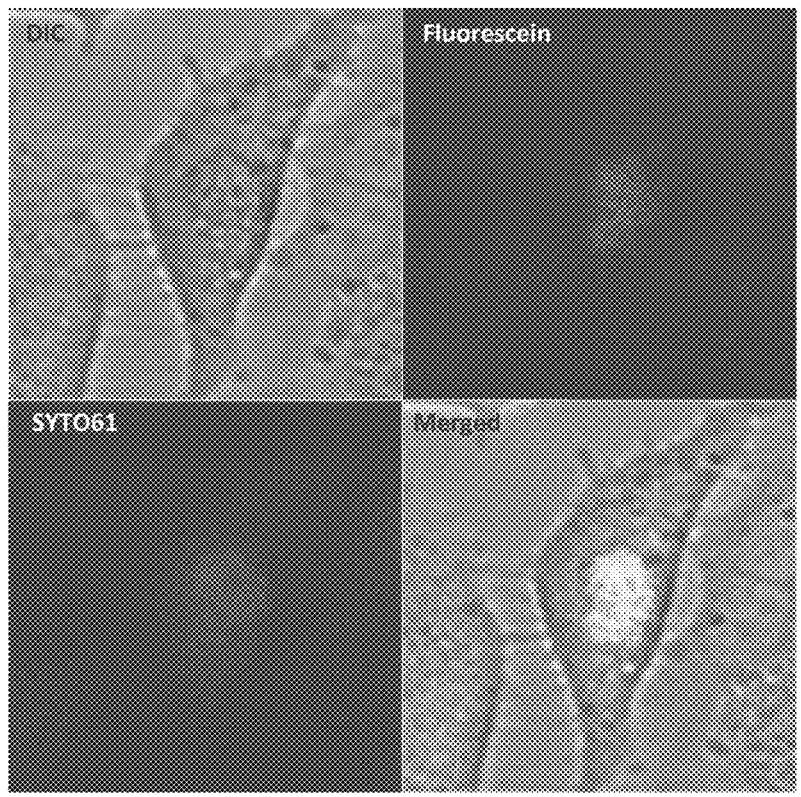
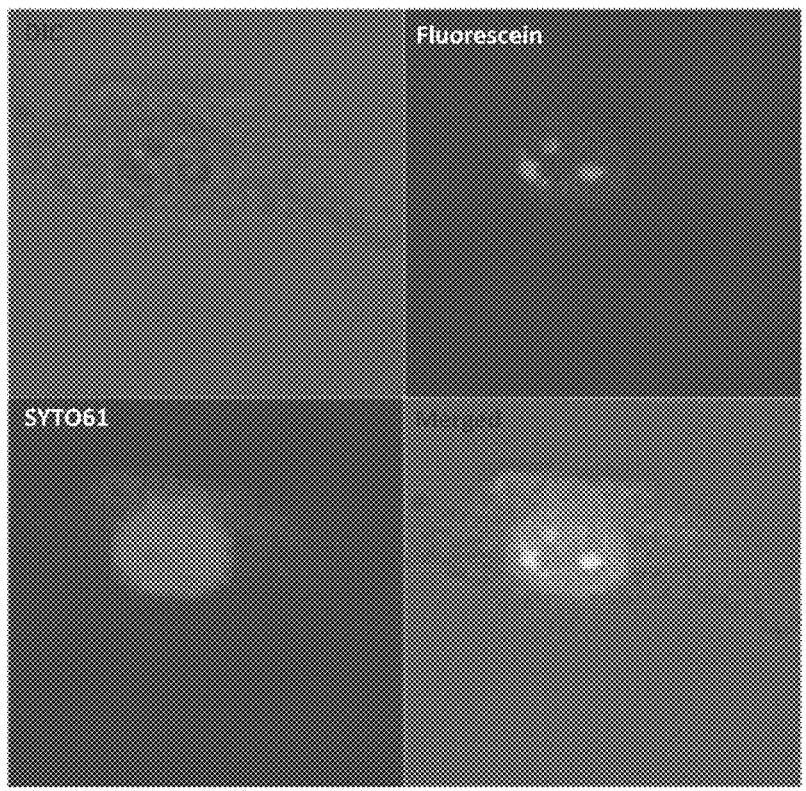

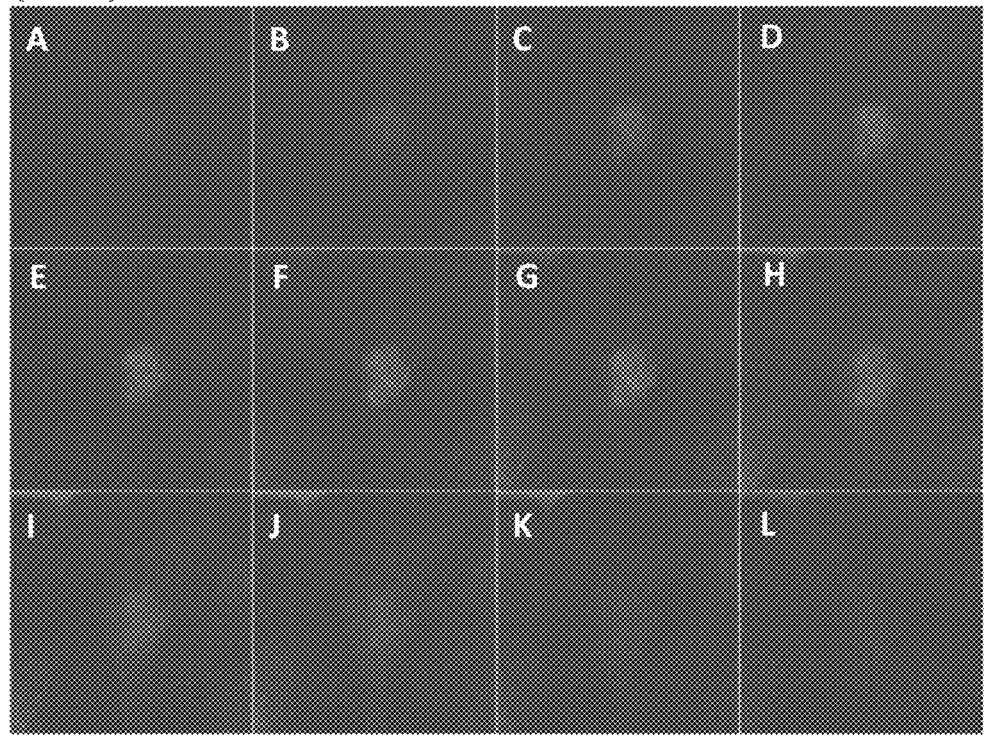
[FIG. 13]

SEQUENCE LISTING

```
<160> NUMBER OF SEQ ID NOS: 64

<210> SEQ ID NO 1
<211> LENGTH: 24
<212> TYPE: RNA
<213> ORGANISM: Artificial
<220> FEATURE:
<223> OTHER INFORMATION: Synthesized RNA.
<220> FEATURE:
<221> NAME/KEY: misc_feature
<222> LOCATION: (4)..(5)
<223> OTHER INFORMATION: "n" stands for a, u, g or c.
<220> FEATURE:
<221> NAME/KEY: misc_feature
<222> LOCATION: (4)..(6)
<223> OTHER INFORMATION: "nnu" is repeated 2 to 3 times.
<220> FEATURE:
<221> NAME/KEY: misc_feature
<222> LOCATION: (10)..(11)
<223> OTHER INFORMATION: "n" stands for a, u, g or c.
<220> FEATURE:
<221> NAME/KEY: misc_feature
<222> LOCATION: (10)..(12)
<223> OTHER INFORMATION: "nnu" is repeated 5 to 7 times.
<220> FEATURE:
<221> NAME/KEY: misc_feature
<222> LOCATION: (16)..(17)
<223> OTHER INFORMATION: "n" stands for a, u, g or c.
<220> FEATURE:
<221> NAME/KEY: misc_feature
<222> LOCATION: (16)..(18)
<223> OTHER INFORMATION: "nnu" is repeated 2 to 3 times.

<400> SEQUENCE: 1
augnnuaugn nuaugnnuug uggc                                             24

<210> SEQ ID NO 2
<211> LENGTH: 21
<212> TYPE: RNA
<213> ORGANISM: Artificial
<220> FEATURE:
<223> OTHER INFORMATION: Synthesized RNA.
<220> FEATURE:
<221> NAME/KEY: misc_feature
```

```
<222> LOCATION: (4)..(5)
<223> OTHER INFORMATION: "n" stands for a, u, g or c.
<220> FEATURE:
<221> NAME/KEY: misc_feature
<222> LOCATION: (4)..(6)
<223> OTHER INFORMATION: "nnu" is repeated 2 to 4 times.
<220> FEATURE:
<221> NAME/KEY: misc_feature
<222> LOCATION: (10)..(11)
<223> OTHER INFORMATION: "n" stands for a, u, g or c.
<220> FEATURE:
<221> NAME/KEY: misc_feature
<222> LOCATION: (10)..(12)
<223> OTHER INFORMATION: "nnu" is repeated 5 to 7 times.

<400> SEQUENCE: 2
augnnnaugn nnaugugugg c                                                21

<210> SEQ ID NO 3
<211> LENGTH: 14
<212> TYPE: PRT
<213> ORGANISM: Artificial
<220> FEATURE:
<223> OTHER INFORMATION: Synthesized peptide.
<220> FEATURE:
<221> NAME/KEY: MOD_RES
<222> LOCATION: (1)..(1)
<223> OTHER INFORMATION: Chloroacetyl-D-phenylalanine.
<220> FEATURE:
<221> NAME/KEY: misc_feature
<222> LOCATION: (4)..(4)
<223> OTHER INFORMATION: "Xaa" stands for 2-Aminoheptonic acid.
<220> FEATURE:
<221> NAME/KEY: misc_feature
<222> LOCATION: (11)..(11)
<223> OTHER INFORMATION: "Xaa" stands for 2-Aminoheptonic acid.

<400> SEQUENCE: 3

Phe Asn Ala Xaa Tyr Pro Tyr Arg Pro Pro Xaa Thr Ser Cys
1               5                   10

<210> SEQ ID NO 4
<211> LENGTH: 14
<212> TYPE: PRT
<213> ORGANISM: Artificial
<220> FEATURE:
<223> OTHER INFORMATION: Synthesized peptide.
<220> FEATURE:
<221> NAME/KEY: MOD_RES
<222> LOCATION: (1)..(1)
<223> OTHER INFORMATION: Chloroacetyl-D-phenylalanine.
<220> FEATURE:
<221> NAME/KEY: MISC_FEATURE
<222> LOCATION: (4)..(4)
<223> OTHER INFORMATION: "Xaa" stands for 2-Aminoheptonic acid.
<220> FEATURE:
<221> NAME/KEY: MISC_FEATURE
<222> LOCATION: (11)..(11)
<223> OTHER INFORMATION: "Xaa" stands for 2-Aminoheptonic acid.

<400> SEQUENCE: 4

Phe Asp Ala Xaa Tyr Pro Phe Arg Pro Pro Xaa Ala His Cys
1               5                   10

<210> SEQ ID NO 5
<211> LENGTH: 15
<212> TYPE: PRT
<213> ORGANISM: Artificial
<220> FEATURE:
<223> OTHER INFORMATION: Synthesized peptide.
<220> FEATURE:
<221> NAME/KEY: MOD_RES
<222> LOCATION: (1)..(1)
```

```
<223> OTHER INFORMATION: Chloroacetyl-D-phenylalanine.
<220> FEATURE:
<221> NAME/KEY: MISC_FEATURE
<222> LOCATION: (5)..(5)
<223> OTHER INFORMATION: "Xaa" stands for 2-Aminoheptonic acid.
<220> FEATURE:
<221> NAME/KEY: MISC_FEATURE
<222> LOCATION: (11)..(11)
<223> OTHER INFORMATION: "Xaa" stands for 2-Aminoheptonic acid.

<400> SEQUENCE: 5

Phe Tyr Arg Cys Xaa His Pro Val Pro Val Xaa Pro Thr Pro Cys
1               5                   10                  15

<210> SEQ ID NO 6
<211> LENGTH: 14
<212> TYPE: PRT
<213> ORGANISM: Artificial
<220> FEATURE:
<223> OTHER INFORMATION: Synthesized peptide.
<220> FEATURE:
<221> NAME/KEY: MOD_RES
<222> LOCATION: (1)..(1)
<223> OTHER INFORMATION: Chloroacetyl-D-phenylalanine.
<220> FEATURE:
<221> NAME/KEY: MISC_FEATURE
<222> LOCATION: (4)..(4)
<223> OTHER INFORMATION: "Xaa" stands for 2-Aminoheptonic acid.
<220> FEATURE:
<221> NAME/KEY: MISC_FEATURE
<222> LOCATION: (11)..(11)
<223> OTHER INFORMATION: "Xaa" stands for 2-Aminoheptonic acid.

<400> SEQUENCE: 6

Phe Asn Ala Xaa Tyr Pro Phe Arg Pro Pro Xaa Thr Thr Cys
1               5                   10

<210> SEQ ID NO 7
<211> LENGTH: 15
<212> TYPE: PRT
<213> ORGANISM: Artificial
<220> FEATURE:
<223> OTHER INFORMATION: Synthesized peptide.
<220> FEATURE:
<221> NAME/KEY: MOD_RES
<222> LOCATION: (1)..(1)
<223> OTHER INFORMATION: Chloroacetyl-D-phenylalanine.
<220> FEATURE:
<221> NAME/KEY: MISC_FEATURE
<222> LOCATION: (5)..(5)
<223> OTHER INFORMATION: "Xaa" stands for 2-Aminoheptonic acid.
<220> FEATURE:
<221> NAME/KEY: MISC_FEATURE
<222> LOCATION: (11)..(11)
<223> OTHER INFORMATION: "Xaa" stands for 2-Aminoheptonic acid.

<400> SEQUENCE: 7

Phe Tyr Arg Cys Xaa Tyr Pro Val Pro Arg Xaa Thr Arg Pro Cys
1               5                   10                  15

<210> SEQ ID NO 8
<211> LENGTH: 17
<212> TYPE: PRT
<213> ORGANISM: Artificial
<220> FEATURE:
<223> OTHER INFORMATION: Synthesized peptide.
<220> FEATURE:
<221> NAME/KEY: MOD_RES
<222> LOCATION: (1)..(1)
<223> OTHER INFORMATION: Chloroacetyl-D-phenylalanine.
<220> FEATURE:
<221> NAME/KEY: MISC_FEATURE
<222> LOCATION: (5)..(5)
```

<223> OTHER INFORMATION: "Xaa" stands for 2-Aminoheptonic acid.
<220> FEATURE:
<221> NAME/KEY: MISC_FEATURE
<222> LOCATION: (13)..(13)
<223> OTHER INFORMATION: "Xaa" stands for 2-Aminoheptonic acid.

<400> SEQUENCE: 8

Phe Tyr Arg Cys Xaa Tyr Pro Leu Pro Ser Pro Pro Xaa Thr Pro His
1               5                   10                  15

Cys

<210> SEQ ID NO 9
<211> LENGTH: 14
<212> TYPE: PRT
<213> ORGANISM: Artificial
<220> FEATURE:
<223> OTHER INFORMATION: Synthesized peptide.
<220> FEATURE:
<221> NAME/KEY: MOD_RES
<222> LOCATION: (1)..(1)
<223> OTHER INFORMATION: Chloroacetyl-D-phenylalanine.
<220> FEATURE:
<221> NAME/KEY: MISC_FEATURE
<222> LOCATION: (5)..(5)
<223> OTHER INFORMATION: "Xaa" stands for 2-Aminoheptonic acid.
<220> FEATURE:
<221> NAME/KEY: MISC_FEATURE
<222> LOCATION: (13)..(13)
<223> OTHER INFORMATION: "Xaa" stands for 2-Aminoheptonic acid.

<400> SEQUENCE: 9

Phe Tyr Arg Cys Xaa Tyr Pro Ile Pro Arg Pro Pro Xaa Cys
1               5                   10

<210> SEQ ID NO 10
<211> LENGTH: 14
<212> TYPE: PRT
<213> ORGANISM: Artificial
<220> FEATURE:
<223> OTHER INFORMATION: Synthesized peptide.
<220> FEATURE:
<221> NAME/KEY: MOD_RES
<222> LOCATION: (1)..(1)
<223> OTHER INFORMATION: Chloroacetyl-D-phenylalanine.
<220> FEATURE:
<221> NAME/KEY: MISC_FEATURE
<222> LOCATION: (5)..(5)
<223> OTHER INFORMATION: "Xaa" stands for 2-Aminoheptonic acid.
<220> FEATURE:
<221> NAME/KEY: MISC_FEATURE
<222> LOCATION: (13)..(13)
<223> OTHER INFORMATION: "Xaa" stands for 2-Aminoheptonic acid.

<400> SEQUENCE: 10

Phe Tyr Arg Cys Xaa Asn Pro Ile Pro Ala Leu Pro Xaa Cys
1               5                   10

<210> SEQ ID NO 11
<211> LENGTH: 14
<212> TYPE: PRT
<213> ORGANISM: Artificial
<220> FEATURE:
<223> OTHER INFORMATION: Synthesized peptide.
<220> FEATURE:
<221> NAME/KEY: MOD_RES
<222> LOCATION: (1)..(1)
<223> OTHER INFORMATION: Chloroacetyl-D-phenylalanine.
<220> FEATURE:
<221> NAME/KEY: MISC_FEATURE
<222> LOCATION: (5)..(5)
<223> OTHER INFORMATION: "Xaa" stands for 2-Aminoheptonic acid.
<220> FEATURE:

```
<221> NAME/KEY: MISC_FEATURE
<222> LOCATION: (13)..(13)
<223> OTHER INFORMATION: "Xaa" stands for 2-Aminoheptonic acid.

<400> SEQUENCE: 11

Phe Tyr Arg Cys Xaa His Pro Val Pro Arg Pro Pro Xaa Cys
1               5                   10

<210> SEQ ID NO 12
<211> LENGTH: 15
<212> TYPE: PRT
<213> ORGANISM: Artificial
<220> FEATURE:
<223> OTHER INFORMATION: Synthesized peptide.
<220> FEATURE:
<221> NAME/KEY: MOD_RES
<222> LOCATION: (1)..(1)
<223> OTHER INFORMATION: Chloroacetyl-D-phenylalanine.
<220> FEATURE:
<221> NAME/KEY: MISC_FEATURE
<222> LOCATION: (6)..(6)
<223> OTHER INFORMATION: "Xaa" stands for 2-Aminoheptonic acid.
<220> FEATURE:
<221> NAME/KEY: MISC_FEATURE
<222> LOCATION: (14)..(14)
<223> OTHER INFORMATION: "Xaa" stands for 2-Aminoheptonic acid.

<400> SEQUENCE: 12

Phe Val Ser Arg Ser Xaa Phe Asp Ala Leu Pro Asn Asn Xaa Cys
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthesized peptide.
<220> FEATURE:
<221> NAME/KEY: MOD_RES
<222> LOCATION: (1)..(1)
<223> OTHER INFORMATION: Chloroacetyl-D-phenylalanine.
<220> FEATURE:
<221> NAME/KEY: MISC_FEATURE
<222> LOCATION: (6)..(6)
<223> OTHER INFORMATION: "Xaa" stands for 2-Aminoheptonic acid.
<220> FEATURE:
<221> NAME/KEY: MISC_FEATURE
<222> LOCATION: (14)..(14)
<223> OTHER INFORMATION: "Xaa" stands for 2-Aminoheptonic acid.

<400> SEQUENCE: 13

Phe Pro Ser Ile Arg Xaa Ala Phe Pro His Thr Asn Pro Xaa Cys
1               5                   10                  15

<210> SEQ ID NO 14
<211> LENGTH: 49
<212> TYPE: DNA
<213> ORGANISM: Artificial
<220> FEATURE:
<223> OTHER INFORMATION: Synthesized primer.

<400> SEQUENCE: 14
gtaatacgac tcactatagg cggggtggag cagcctggta gctcgtcgg            49

<210> SEQ ID NO 15
<211> LENGTH: 44
<212> TYPE: DNA
<213> ORGANISM: Artificial
<220> FEATURE:
<223> OTHER INFORMATION: Synthesized primer.
```

<400> SEQUENCE: 15
gaaccgacga tcttcgggtt atgagcccga cgagctacca gcct          44

<210> SEQ ID NO 16
<211> LENGTH: 22
<212> TYPE: DNA
<213> ORGANISM: Artificial
<220> FEATURE:
<223> OTHER INFORMATION: Synthesized primer.

<400> SEQUENCE: 16
ggcgtaatac gactcactat ag          22

<210> SEQ ID NO 17
<211> LENGTH: 38
<212> TYPE: DNA
<213> ORGANISM: Artificial
<220> FEATURE:
<223> OTHER INFORMATION: Synthesized primer.

<400> SEQUENCE: 17
tggttgcggg ggccggattt gaaccgacga tcttcggg          38

<210> SEQ ID NO 18
<211> LENGTH: 20
<212> TYPE: DNA
<213> ORGANISM: Artificial
<220> FEATURE:
<223> OTHER INFORMATION: Synthesized primer.

<400> SEQUENCE: 18
tggttgcggg ggcccgattt          20

<210> SEQ ID NO 19
<211> LENGTH: 49
<212> TYPE: DNA
<213> ORGANISM: Artificial
<220> FEATURE:
<223> OTHER INFORMATION: Synthesized primer.

<400> SEQUENCE: 19
gtaatacgac tcactatagg ctctgtagtt cagtcggtag aacggcgga          49

<210> SEQ ID NO 20
<211> LENGTH: 43
<212> TYPE: DNA
<213> ORGANISM: Artificial
<220> FEATURE:
<223> OTHER INFORMATION: Synthesized primer.

<400> SEQUENCE: 20
gaaccagtga catacggatt atgagtccgc cgttctaccg act          43

<210> SEQ ID NO 21
<211> LENGTH: 38
<212> TYPE: DNA
<213> ORGANISM: Artificial
<220> FEATURE:
<223> OTHER INFORMATION: Synthesized primer.

<400> SEQUENCE: 21
tggcggctct gactggactc gaaccagtga catacgga          38

<210> SEQ ID NO 22
<211> LENGTH: 20

<212> TYPE: DNA
<213> ORGANISM: Artificial
<220> FEATURE:
<223> OTHER INFORMATION: Synthesized primer.

<400> SEQUENCE: 22
tggcggctct gactggactc                                            20

<210> SEQ ID NO 23
<211> LENGTH: 36
<212> TYPE: DNA
<213> ORGANISM: Artificial
<220> FEATURE:
<223> OTHER INFORMATION: Synthesized primer.

<400> SEQUENCE: 23
gtaatacgac tcactatagg atcgaaagat ttccgc                          36

<210> SEQ ID NO 24
<211> LENGTH: 45
<212> TYPE: DNA
<213> ORGANISM: Artificial
<220> FEATURE:
<223> OTHER INFORMATION: Synthesized primer.

<400> SEQUENCE: 24
acctaacgct aatccccttt cggggccgcg gaaatctttc gatcc                45

<210> SEQ ID NO 25
<211> LENGTH: 18
<212> TYPE: DNA
<213> ORGANISM: Artificial
<220> FEATURE:
<223> OTHER INFORMATION: Synthesized primer.

<400> SEQUENCE: 25
acctaacgct aatcccct                                              18

<210> SEQ ID NO 26
<211> LENGTH: 43
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (21)..(21)
<223> OTHER INFORMATION: "n" stands for uracil.

<400> SEQUENCE: 26
gaaccagtga catacggatt nggagtccgc cgttctaccg act                  43

<210> SEQ ID NO 27
<211> LENGTH: 46
<212> TYPE: DNA
<213> ORGANISM: Artificial
<220> FEATURE:
<223> OTHER INFORMATION: Synthesized primer.

<400> SEQUENCE: 27
taatacgact cactataggg ttaactttaa caaggagaaa aacatg               46

<210> SEQ ID NO 28
<211> LENGTH: 47
<212> TYPE: DNA
<213> ORGANISM: Artificial
<220> FEATURE:

<223> OTHER INFORMATION: Synthesized primer.

<400> SEQUENCE: 28
aatcggcgga atagacttgg tcatcatgtt tttctccttg ttaaagt    47

<210> SEQ ID NO 29
<211> LENGTH: 22
<212> TYPE: DNA
<213> ORGANISM: Artificial
<220> FEATURE:
<223> OTHER INFORMATION: Synthesized primer.

<400> SEQUENCE: 29
ggcgtaatac gactcactat ag    22

<210> SEQ ID NO 30
<211> LENGTH: 49
<212> TYPE: DNA
<213> ORGANISM: Artificial
<220> FEATURE:
<223> OTHER INFORMATION: Synthesized primer.

<400> SEQUENCE: 30
cgtcgtcctt gtagtcacag tccggaaaca taatcggcgg aatagactt    49

<210> SEQ ID NO 31
<211> LENGTH: 29
<212> TYPE: DNA
<213> ORGANISM: Artificial
<220> FEATURE:
<223> OTHER INFORMATION: Synthesized primer.

<400> SEQUENCE: 31
ttacttgtcg tcgtcgtcct tgtagtcac    29

<210> SEQ ID NO 32
<211> LENGTH: 49
<212> TYPE: DNA
<213> ORGANISM: Artificial
<220> FEATURE:
<223> OTHER INFORMATION: Synthesized primer.

<400> SEQUENCE: 32
taatacgact cactataggg ttgaacttta agtaggagat atatccatg    49

<210> SEQ ID NO 33
<211> LENGTH: 39
<212> TYPE: DNA
<213> ORGANISM: Artificial
<220> FEATURE:
<223> OTHER INFORMATION: Synthesized primer.

<400> SEQUENCE: 33
tttccgcccc ccgtcctaag acccagaccc agacccaca    39

<210> SEQ ID NO 34
<211> LENGTH: 78
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (23)..(24)
<223> OTHER INFORMATION: "n" stands for a, c, g or t.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (32)..(33)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (41)..(42)
<223> OTHER INFORMATION: "n" stands for a, c, g or t.
<220> FEATURE:
<221> NAME/KEY: misc_feature
<222> LOCATION: (44)..(45)
<223> OTHER INFORMATION: "n" stands for a, c, g or t.
<220> FEATURE:
<221> NAME/KEY: misc_feature
<222> LOCATION: (50)..(51)
<223> OTHER INFORMATION: "n" stands for a, c, g or t.
<220> FEATURE:
<221> NAME/KEY: misc_feature
<222> LOCATION: (53)..(54)
<223> OTHER INFORMATION: "n" stands for a, c, g or t.

<400> SEQUENCE: 34
agacccagac ccagacccac aannanncat annannanna nnanncatan nanncatgga    60
tatatctcct acttaaag                                                  78

<210> SEQ ID NO 35
<211> LENGTH: 81
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (23)..(24)
<223> OTHER INFORMATION: "n" stands for a, c, g or t.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (32)..(33)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (41)..(42)
<223> OTHER INFORMATION: "n" stands for a, c, g or t.
<220> FEATURE:
<221> NAME/KEY: misc_feature
<222> LOCATION: (44)..(45)
<223> OTHER INFORMATION: "n" stands for a, c, g or t.
<220> FEATURE:
<221> NAME/KEY: misc_feature
<222> LOCATION: (47)..(48)
<223> OTHER INFORMATION: "n" stands for a, c, g or t.
<220> FEATURE:
<221> NAME/KEY: misc_feature
<222> LOCATION: (53)..(54)

<223> OTHER INFORMATION: "n" stands for a, c, g or t.
<220> FEATURE:
<221> NAME/KEY: misc_feature
<222> LOCATION: (56)..(57)
<223> OTHER INFORMATION: "n" stands for a, c, g or t.

<400> SEQUENCE: 35
agacccagac ccagacccac aannanncat annannanna nnannannca tannannncat    60 ggatatatct cctacttaaa g                                               81

<210> SEQ ID NO 36
<211> LENGTH: 83
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (23)..(24)
<223> OTHER INFORMATION: "n" stands for a, c, g or t.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (32)..(33)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (41)..(44)
<223> OTHER INFORMATION: "n" stands for a, c, g or t.
<220> FEATURE:
<221> NAME/KEY: misc_feature
<222> LOCATION: (46)..(47)
<223> OTHER INFORMATION: "n" stands for a, c, g or t.
<220> FEATURE:
<221> NAME/KEY: misc_feature
<222> LOCATION: (49)..(50)
<223> OTHER INFORMATION: "n" stands for a, c, g or t.
<220> FEATURE:
<221> NAME/KEY: misc_feature
<222> LOCATION: (55)..(56)
<223> OTHER INFORMATION: "n" stands for a, c, g or t.
<220> FEATURE:
<221> NAME/KEY: misc_feature
<222> LOCATION: (58)..(59)
<223> OTHER INFORMATION: "n" stands for a, c, g or t.

<400> SEQUENCE: 36
agacccagac ccagacccac aannanncat annannanna nnnnannann catannannc     60
atggatatat ctcctactta aag                                             83

<210> SEQ ID NO 37
<211> LENGTH: 81
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (23)..(24)
<223> OTHER INFORMATION: "n" stands for a, c, g or t.
<220> FEATURE:
<221> NAME/KEY: misc_feature

```
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (41)..(42)
<223> OTHER INFORMATION: "n" stands for a, c, g or t.
<220> FEATURE:
<221> NAME/KEY: misc_feature
<222> LOCATION: (44)..(45)
<223> OTHER INFORMATION: "n" stands for a, c, g or t.
<220> FEATURE:
<221> NAME/KEY: misc_feature
<222> LOCATION: (47)..(48)
<223> OTHER INFORMATION: "n" stands for a, c, g or t.
<220> FEATURE:
<221> NAME/KEY: misc_feature
<222> LOCATION: (53)..(54)
<223> OTHER INFORMATION: "n" stands for a, c, g or t.
<220> FEATURE:
<221> NAME/KEY: misc_feature
<222> LOCATION: (56)..(57)
<223> OTHER INFORMATION: "n" stands for a, c, g or t.

<400> SEQUENCE: 37
agacccagac ccagacccac aannannann catannanna nnannannca tannanncat    60
ggatatatct cctacttaaa g                                              81

<210> SEQ ID NO 38
<211> LENGTH: 84
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (23)..(24)
<223> OTHER INFORMATION: "n" stands for a, c, g or t.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (41)..(42)
<223> OTHER INFORMATION: "n" stands for a, c, g or t.
<220> FEATURE:
<221> NAME/KEY: misc_feature
<222> LOCATION: (44)..(45)
<223> OTHER INFORMATION: "n" stands for a, c, g or t.
<220> FEATURE:
<221> NAME/KEY: misc_feature
<222> LOCATION: (47)..(48)
```

<223> OTHER INFORMATION: "n" stands for a, c, g or t.
<220> FEATURE:
<221> NAME/KEY: misc_feature
<222> LOCATION: (50)..(51)
<223> OTHER INFORMATION: "n" stands for a, c, g or t.
<220> FEATURE:
<221> NAME/KEY: misc_feature
<222> LOCATION: (56)..(57)
<223> OTHER INFORMATION: "n" stands for a, c, g or t.
<220> FEATURE:
<221> NAME/KEY: misc_feature
<222> LOCATION: (59)..(60)
<223> OTHER INFORMATION: "n" stands for a, c, g or t.

<400> SEQUENCE: 38
agacccagac ccagacccac aannannann catannanna nnannannan ncatannann    60
catggatata tctcctactt aaag                                           84

<210> SEQ ID NO 39
<211> LENGTH: 86
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (23)..(24)
<223> OTHER INFORMATION: "n" stands for a, c, g or t.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (41)..(42)
<223> OTHER INFORMATION: "n" stands for a, c, g or t.
<220> FEATURE:
<221> NAME/KEY: misc_feature
<222> LOCATION: (44)..(45)
<223> OTHER INFORMATION: "n" stands for a, c, g or t.
<220> FEATURE:
<221> NAME/KEY: misc_feature
<222> LOCATION: (47)..(48)
<223> OTHER INFORMATION: "n" stands for a, c, g or t.
<220> FEATURE:
<221> NAME/KEY: misc_feature
<222> LOCATION: (50)..(51)
<223> OTHER INFORMATION: "n" stands for a, c, g or t.
<220> FEATURE:
<221> NAME/KEY: misc_feature
<222> LOCATION: (53)..(54)
<223> OTHER INFORMATION: "n" stands for a, c, g or t.
<220> FEATURE:
<221> NAME/KEY: misc_feature
<222> LOCATION: (59)..(60)
<223> OTHER INFORMATION: "n" stands for a, c, g or t.
<220> FEATURE:
<221> NAME/KEY: misc_feature
<222> LOCATION: (62)..(63)
<223> OTHER INFORMATION: "n" stands for a, c, g or t.

<400> SEQUENCE: 39
agacccagac ccagacccac aannannann catannanna nnannannan nanncatann    60
anncatggat atatctccta cttaaa                                          86

<210> SEQ ID NO 40
<211> LENGTH: 84
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (23)..(24)
<223> OTHER INFORMATION: "n" stands for a, c, g or t.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (41)..(42)
<223> OTHER INFORMATION: "n" stands for a, c, g or t.
<220> FEATURE:
<221> NAME/KEY: misc_feature
<222> LOCATION: (44)..(45)
<223> OTHER INFORMATION: "n" stands for a, c, g or t.
<220> FEATURE:
<221> NAME/KEY: misc_feature
<222> LOCATION: (47)..(48)
<223> OTHER INFORMATION: "n" stands for a, c, g or t.
<220> FEATURE:
<221> NAME/KEY: misc_feature
<222> LOCATION: (53)..(54)
<223> OTHER INFORMATION: "n" stands for a, c, g or t.
<220> FEATURE:
<221> NAME/KEY: misc_feature
<222> LOCATION: (56)..(57)
<223> OTHER INFORMATION: "n" stands for a, c, g or t.
<220> FEATURE:
<221> NAME/KEY: misc_feature
<222> LOCATION: (59)..(60)
<223> OTHER INFORMATION: "n" stands for a, c, g or t.

<400> SEQUENCE: 40
agacccagac ccagacccac aannannann catannanna nnannannca tannannann    60
catggatata tctcctactt aaag                                           84

<210> SEQ ID NO 41
<211> LENGTH: 87
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (23)..(24)
<223> OTHER INFORMATION: "n" stands for a, c, g or t.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)

<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (41)..(42)
<223> OTHER INFORMATION: "n" stands for a, c, g or t.
<220> FEATURE:
<221> NAME/KEY: misc_feature
<222> LOCATION: (44)..(45)
<223> OTHER INFORMATION: "n" stands for a, c, g or t.
<220> FEATURE:
<221> NAME/KEY: misc_feature
<222> LOCATION: (47)..(48)
<223> OTHER INFORMATION: "n" stands for a, c, g or t.
<220> FEATURE:
<221> NAME/KEY: misc_feature
<222> LOCATION: (50)..(51)
<223> OTHER INFORMATION: "n" stands for a, c, g or t.
<220> FEATURE:
<221> NAME/KEY: misc_feature
<222> LOCATION: (56)..(57)
<223> OTHER INFORMATION: "n" stands for a, c, g or t.
<220> FEATURE:
<221> NAME/KEY: misc_feature
<222> LOCATION: (59)..(60)
<223> OTHER INFORMATION: "n" stands for a, c, g or t.
<220> FEATURE:
<221> NAME/KEY: misc_feature
<222> LOCATION: (62)..(63)
<223> OTHER INFORMATION: "n" stands for a, c, g or t.

<400> SEQUENCE: 41
agacccagac ccagacccac aannannann catannanna nnannannan ncatannann    60
anncatggat atatctccta cttaaag                                        87

<210> SEQ ID NO 42
<211> LENGTH: 89
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (23)..(24)
<223> OTHER INFORMATION: "n" stands for a, c, g or t.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (41)..(42)
<223> OTHER INFORMATION: "n" stands for a, c, g or t.
<220> FEATURE:
<221> NAME/KEY: misc_feature
<222> LOCATION: (44)..(45)
<223> OTHER INFORMATION: "n" stands for a, c, g or t.

<220> FEATURE:
<221> NAME/KEY: misc_feature
<222> LOCATION: (47)..(48)
<223> OTHER INFORMATION: "n" stands for a, c, g or t.
<220> FEATURE:
<221> NAME/KEY: misc_feature
<222> LOCATION: (50)..(51)
<223> OTHER INFORMATION: "n" stands for a, c, g or t.
<220> FEATURE:
<221> NAME/KEY: misc_feature
<222> LOCATION: (53)..(54)
<223> OTHER INFORMATION: "n" stands for a, c, g or t.
<220> FEATURE:
<221> NAME/KEY: misc_feature
<222> LOCATION: (59)..(60)
<223> OTHER INFORMATION: "n" stands for a, c, g or t.
<220> FEATURE:
<221> NAME/KEY: misc_feature
<222> LOCATION: (62)..(63)
<223> OTHER INFORMATION: "n" stands for a, c, g or t.
<220> FEATURE:
<221> NAME/KEY: misc_feature
<222> LOCATION: (65)..(66)
<223> OTHER INFORMATION: "n" stands for a, c, g or t.

<400> SEQUENCE: 42
agacccagac ccagacccac aannannann catannanna nnannannan nanncatann    60
annanncatg gatatatctc ctacttaag                                      89

<210> SEQ ID NO 43
<211> LENGTH: 72
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)
<223> OTHER INFORMATION: "n" stands for a, c, g or t.
<220> FEATURE:
<221> NAME/KEY: misc_feature
<222> LOCATION: (32)..(33)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (44)..(45)
<223> OTHER INFORMATION: "n" stands for a, c, g or t.
<220> FEATURE:
<221> NAME/KEY: misc_feature
<222> LOCATION: (47)..(48)
<223> OTHER INFORMATION: "n" stands for a, c, g or t.

<400> SEQUENCE: 43
agacccagac ccagacccac acatannann annannannc atannannca tggatatatc    60
tcctacttaa ag                                                        72

<210> SEQ ID NO 44
<211> LENGTH: 75
<212> TYPE: DNA
<213> ORGANISM: Artificial
<220> FEATURE:

<223> OTHER INFORMATION: Synthesized primer.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)
<223> OTHER INFORMATION: "n" stands for a, c, g or t.
<220> FEATURE:
<221> NAME/KEY: misc_feature
<222> LOCATION: (32)..(33)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (41)..(42)
<223> OTHER INFORMATION: "n" stands for a, c, g or t.
<220> FEATURE:
<221> NAME/KEY: misc_feature
<222> LOCATION: (47)..(48)
<223> OTHER INFORMATION: "n" stands for a, c, g or t.
<220> FEATURE:
<221> NAME/KEY: misc_feature
<222> LOCATION: (50)..(51)
<223> OTHER INFORMATION: "n" stands for a, c, g or t.

<400> SEQUENCE: 44
agacccagac ccagacccac acatannann annannanna nncatannan ncatggatat    60
atctcctact taaag                                                    75

<210> SEQ ID NO 45
<211> LENGTH: 78
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)
<223> OTHER INFORMATION: "n" stands for a, c, g or t.
<220> FEATURE:
<221> NAME/KEY: misc_feature
<222> LOCATION: (32)..(33)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (41)..(42)
<223> OTHER INFORMATION: "n" stands for a, c, g or t.
<220> FEATURE:
<221> NAME/KEY: misc_feature
<222> LOCATION: (44)..(45)
<223> OTHER INFORMATION: "n" stands for a, c, g or t.
<220> FEATURE:
<221> NAME/KEY: misc_feature
<222> LOCATION: (50)..(51)
<223> OTHER INFORMATION: "n" stands for a, c, g or t.

```
<220> FEATURE:
<221> NAME/KEY: misc_feature
<222> LOCATION: (53)..(54)
<223> OTHER INFORMATION: "n" stands for a, c, g or t.

<400> SEQUENCE: 45
agacccagac ccagacccac acatannann annannanna nnanncatan nanncatgga    60
tatatctcct acttaaag                                                  78

<210> SEQ ID NO 46
<211> LENGTH: 75
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)
<223> OTHER INFORMATION: "n" stands for a, c, g or t.
<220> FEATURE:
<221> NAME/KEY: misc_feature
<222> LOCATION: (32)..(33)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (44)..(45)
<223> OTHER INFORMATION: "n" stands for a, c, g or t.
<220> FEATURE:
<221> NAME/KEY: misc_feature
<222> LOCATION: (47)..(48)
<223> OTHER INFORMATION: "n" stands for a, c, g or t.
<220> FEATURE:
<221> NAME/KEY: misc_feature
<222> LOCATION: (50)..(51)
<223> OTHER INFORMATION: "n" stands for a, c, g or t.

<400> SEQUENCE: 46
agacccagac ccagacccac acatannann annannannc atannannan ncatggatat    60
atctcctact taaag                                                     75

<210> SEQ ID NO 47
<211> LENGTH: 78
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)
<223> OTHER INFORMATION: "n" stands for a, c, g or t.
<220> FEATURE:
<221> NAME/KEY: misc_feature
<222> LOCATION: (32)..(33)
<223> OTHER INFORMATION: "n" stands for a, c, g or t.
<220> FEATURE:
<221> NAME/KEY: misc_feature
<222> LOCATION: (35)..(36)
```

```
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (41)..(42)
<223> OTHER INFORMATION: "n" stands for a, c, g or t.
<220> FEATURE:
<221> NAME/KEY: misc_feature
<222> LOCATION: (47)..(48)
<223> OTHER INFORMATION: "n" stands for a, c, g or t.
<220> FEATURE:
<221> NAME/KEY: misc_feature
<222> LOCATION: (50)..(51)
<223> OTHER INFORMATION: "n" stands for a, c, g or t.
<220> FEATURE:
<221> NAME/KEY: misc_feature
<222> LOCATION: (53)..(54)
<223> OTHER INFORMATION: "n" stands for a, c, g or t.

<400> SEQUENCE: 47
agacccagac ccagacccac acatannann annannanna nncatannan nanncatgga    60
tatatctcct acttaaag                                                  78

<210> SEQ ID NO 48
<211> LENGTH: 81
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)
<223> OTHER INFORMATION: "n" stands for a, c, g or t.
<220> FEATURE:
<221> NAME/KEY: misc_feature
<222> LOCATION: (32)..(33)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (41)..(42)
<223> OTHER INFORMATION: "n" stands for a, c, g or t.
<220> FEATURE:
<221> NAME/KEY: misc_feature
<222> LOCATION: (44)..(45)
<223> OTHER INFORMATION: "n" stands for a, c, g or t.
<220> FEATURE:
<221> NAME/KEY: misc_feature
<222> LOCATION: (50)..(51)
<223> OTHER INFORMATION: "n" stands for a, c, g or t.
<220> FEATURE:
<221> NAME/KEY: misc_feature
<222> LOCATION: (53)..(54)
<223> OTHER INFORMATION: "n" stands for a, c, g or t.
<220> FEATURE:
<221> NAME/KEY: misc_feature
<222> LOCATION: (56)..(57)
<223> OTHER INFORMATION: "n" stands for a, c, g or t.

<400> SEQUENCE: 48
agacccagac ccagacccac acatannann annannanna nnanncatan nannanncat    60
```
ggatatatct cctacttaaa g                                                    81

<210> SEQ ID NO 49
<211> LENGTH: 78
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)
<223> OTHER INFORMATION: "n" stands for a, c, g or t.
<220> FEATURE:
<221> NAME/KEY: misc_feature
<222> LOCATION: (32)..(33)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (44)..(45)
<223> OTHER INFORMATION: "n" stands for a, c, g or t.
<220> FEATURE:
<221> NAME/KEY: misc_feature
<222> LOCATION: (47)..(48)
<223> OTHER INFORMATION: "n" stands for a, c, g or t.
<220> FEATURE:
<221> NAME/KEY: misc_feature
<222> LOCATION: (50)..(51)
<223> OTHER INFORMATION: "n" stands for a, c, g or t.
<220> FEATURE:
<221> NAME/KEY: misc_feature
<222> LOCATION: (53)..(54)
<223> OTHER INFORMATION: "n" stands for a, c, g or t.

<400> SEQUENCE: 49
agacccagac ccagacccac acatannann annannannc atannannan nanncatgga         60
tatatctcct acttaaag                                                       78

<210> SEQ ID NO 50
<211> LENGTH: 81
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)
<223> OTHER INFORMATION: "n" stands for a, c, g or t.
<220> FEATURE:
<221> NAME/KEY: misc_feature
<222> LOCATION: (32)..(33)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)

<223> OTHER INFORMATION: "n" stands for a, c, g or t.
<220> FEATURE:
<221> NAME/KEY: misc_feature
<222> LOCATION: (41)..(42)
<223> OTHER INFORMATION: "n" stands for a, c, g or t.
<220> FEATURE:
<221> NAME/KEY: misc_feature
<222> LOCATION: (47)..(48)
<223> OTHER INFORMATION: "n" stands for a, c, g or t.
<220> FEATURE:
<221> NAME/KEY: misc_feature
<222> LOCATION: (50)..(51)
<223> OTHER INFORMATION: "n" stands for a, c, g or t.
<220> FEATURE:
<221> NAME/KEY: misc_feature
<222> LOCATION: (53)..(54)
<223> OTHER INFORMATION: "n" stands for a, c, g or t.
<220> FEATURE:
<221> NAME/KEY: misc_feature
<222> LOCATION: (56)..(57)
<223> OTHER INFORMATION: "n" stands for a, c, g or t.

<400> SEQUENCE: 50
agacccagac ccagacccac acatannann annannanna nncatannan nannanncat      60
ggatatatct cctacttaaa g                                                81

<210> SEQ ID NO 51
<211> LENGTH: 84
<212> TYPE: DNA
<213> ORGANISM: Artificial
<220> FEATURE:
<223> OTHER INFORMATION: Synthesized primer.
<220> FEATURE:
<221> NAME/KEY: misc_feature
<222> LOCATION: (26)..(27)
<223> OTHER INFORMATION: "n" stands for a, c, g or t.
<220> FEATURE:
<221> NAME/KEY: misc_feature
<222> LOCATION: (29)..(30)
<223> OTHER INFORMATION: "n" stands for a, c, g or t.
<220> FEATURE:
<221> NAME/KEY: misc_feature
<222> LOCATION: (32)..(33)
<223> OTHER INFORMATION: "n" stands for a, c, g or t.
<220> FEATURE:
<221> NAME/KEY: misc_feature
<222> LOCATION: (35)..(36)
<223> OTHER INFORMATION: "n" stands for a, c, g or t.
<220> FEATURE:
<221> NAME/KEY: misc_feature
<222> LOCATION: (38)..(39)
<223> OTHER INFORMATION: "n" stands for a, c, g or t.
<220> FEATURE:
<221> NAME/KEY: misc_feature
<222> LOCATION: (41)..(42)
<223> OTHER INFORMATION: "n" stands for a, c, g or t.
<220> FEATURE:
<221> NAME/KEY: misc_feature
<222> LOCATION: (44)..(45)
<223> OTHER INFORMATION: "n" stands for a, c, g or t.
<220> FEATURE:
<221> NAME/KEY: misc_feature
<222> LOCATION: (50)..(51)
<223> OTHER INFORMATION: "n" stands for a, c, g or t.
<220> FEATURE:
<221> NAME/KEY: misc_feature
<222> LOCATION: (53)..(54)
<223> OTHER INFORMATION: "n" stands for a, c, g or t.
<220> FEATURE:
<221> NAME/KEY: misc_feature
<222> LOCATION: (56)..(57)
<223> OTHER INFORMATION: "n" stands for a, c, g or t.
<220> FEATURE:
<221> NAME/KEY: misc_feature
<222> LOCATION: (59)..(60)
<223> OTHER INFORMATION: "n" stands for a, c, g or t.

<400> SEQUENCE: 51
agacccagac ccagacccac acatannann annannanna nnanncatan nannannann    60
catggatata tctcctactt aaag                                            84

<210> SEQ ID NO 52
<211> LENGTH: 49
<212> TYPE: DNA
<213> ORGANISM: Artificial
<220> FEATURE:
<223> OTHER INFORMATION: Synthesized primer.

<400> SEQUENCE: 52
taatacgact cactataggg ttgaacttta agtaggagat atatccatg                 49

<210> SEQ ID NO 53
<211> LENGTH: 39
<212> TYPE: DNA
<213> ORGANISM: Artificial
<220> FEATURE:
<223> OTHER INFORMATION: Synthesized primer.

<400> SEQUENCE: 53
tttccgcccc ccgtcctaag acccagaccc agacccaca                            39

<210> SEQ ID NO 54
<211> LENGTH: 69
<212> TYPE: RNA
<213> ORGANISM: Artificial
<220> FEATURE:
<223> OTHER INFORMATION: Synthesized DNA.

<400> SEQUENCE: 54
auguggacca agucuauucc gccgauuugg uuuccggacu gugacuacaa ggacgacgac    60
gacaaguaa                                                             69

<210> SEQ ID NO 55
<211> LENGTH: 22
<212> TYPE: PRT
<213> ORGANISM: Artificial
<220> FEATURE:
<223> OTHER INFORMATION: Synthesized peptide.
<220> FEATURE:
<221> NAME/KEY: MOD_RES
<222> LOCATION: (1)..(1)
<223> OTHER INFORMATION: Chloroacetyl-D-phenylalanine.
<220> FEATURE:
<221> NAME/KEY: MISC_FEATURE
<222> LOCATION: (2)..(2)
<223> OTHER INFORMATION: "Xaa" stands for 2-Aminoheptonic acid.
<220> FEATURE:
<221> NAME/KEY: MISC_FEATURE
<222> LOCATION: (10)..(10)
<223> OTHER INFORMATION: "Xaa" stands for 2-Aminoheptonic acid.

<400> SEQUENCE: 55

Phe Xaa Thr Lys Ser Ile Pro Pro Ile Xaa Phe Pro Asp Cys Asp Tyr
1               5                   10                  15

Lys Asp Asp Asp Asp Lys
            20

<210> SEQ ID NO 56
<211> LENGTH: 22
<212> TYPE: PRT
<213> ORGANISM: Artificial
<220> FEATURE:

```
<223> OTHER INFORMATION: Synthesized peptide.
<220> FEATURE:
<221> NAME/KEY: MISC_FEATURE
<222> LOCATION: (1)..(1)
<223> OTHER INFORMATION: Chloroacetyl-D-phenylalanine.

<400> SEQUENCE: 56

Phe Ser Thr Lys Ser Ile Pro Pro Ile Ser Phe Pro Asp Cys Asp Tyr
1               5                   10                  15

Lys Asp Asp Asp Asp Lys
            20

<210> SEQ ID NO 57
<211> LENGTH: 18
<212> TYPE: RNA
<213> ORGANISM: Artificial
<220> FEATURE:
<223> OTHER INFORMATION: Synthesized RNA.

<400> SEQUENCE: 57
uaauacgacu cacuauag                                                 18

<210> SEQ ID NO 58
<211> LENGTH: 10
<212> TYPE: RNA
<213> ORGANISM: Artificial
<220> FEATURE:
<223> OTHER INFORMATION: Synthesized RNA.

<400> SEQUENCE: 58
uuaacuuuaa                                                          10

<210> SEQ ID NO 59
<211> LENGTH: 7
<212> TYPE: RNA
<213> ORGANISM: Artificial
<220> FEATURE:
<223> OTHER INFORMATION: Synthesized RNA.

<400> SEQUENCE: 59 aaggaga                                                              7

<210> SEQ ID NO 60
<211> LENGTH: 18
<212> TYPE: RNA
<213> ORGANISM: Artificial
<220> FEATURE:
<223> OTHER INFORMATION: Synthesized RNA.

<400> SEQUENCE: 60
ggcagcggca gcggcagc                                                 18

<210> SEQ ID NO 61
<211> LENGTH: 18
<212> TYPE: RNA
<213> ORGANISM: Artificial
<220> FEATURE:
<223> OTHER INFORMATION: Synthesized RNA.

<400> SEQUENCE: 61
uaggacgggg ggcggaaa                                                 18

<210> SEQ ID NO 62
<211> LENGTH: 49
<212> TYPE: DNA
<213> ORGANISM: Artificial
```

```
<220> FEATURE:
<223> OTHER INFORMATION: Synthesized primer.

<400> SEQUENCE: 62
taatacgact cactataggg ttgaacttta agtaggagat atatccatg              49

<210> SEQ ID NO 63
<211> LENGTH: 39
<212> TYPE: DNA
<213> ORGANISM: Artificial
<220> FEATURE:
<223> OTHER INFORMATION: Synthesized primer.

<400> SEQUENCE: 63
tttccgcccc ccgtcctaag acccagaccc agacccaca                        39

<210> SEQ ID NO 64
<211> LENGTH: 16
<212> TYPE: DNA
<213> ORGANISM: Artificial
<220> FEATURE:
<223> OTHER INFORMATION: Synthesized DNA.

<400> SEQUENCE: 64
ctcccgcccc ccgtcc                                                  16
```

MACROCYCLIC PEPTIDE, METHOD FOR PRODUCING SAME, AND SCREENING METHOD USING MACROCYCLIC PEPTIDE LIBRARY

REFERENCE TO A SEQUENCE LISTING SUBMITTED VIA EFS-WEB

The content of the ASCII text file of the sequence listing named "20160225_034574_009US1_seq" which is 31.3 kb in size, was downloaded from the WIPO database, has a created date of Sep. 15, 2014, and was electronically submitted via EFS-Web on Feb. 25, 2016, is incorporated herein by reference in its entirety.

TECHNICAL FIELD

The present invention relates to macrocyclic peptides stable in vivo and permeable through cell membranes.

BACKGROUND ART

In recent years, a variety of peptide drugs have been researched and developed. Major advantages of peptide drugs are that they have high affinity and high specificity for target molecules and capable of protein-protein interaction inhibition that has not easily been achieved by low molecular compounds.

Peptide drugs obtained are likely to have higher specificity in interaction with target molecules than low molecular compounds due to their chemical and biological diversity and this leads to their greater physiological activity. With regard to specificity or selectivity, peptide drugs are equivalent to antibody drugs.

Peptide drugs however have a problem that similar to almost all other biopharmaceuticals, they are not so effective because they cannot penetrate cell membranes and therefore cannot reach into the cells and they are degraded in a short time because of inferiority in protease resistance to large proteins such as antibiotics.

Resolution of such a problem of peptide drugs has been investigated recently by adding various modifications to them.

The present inventors previously developed artificial aminoacylated RNA catalyst "flexizyme (flexizyme)" (for example, Non-patent Document 1). Flexizyme is an artificial RNA catalyst having aminoacyl tRNA synthetase-like activity which can link an arbitrary amino acid to an arbitrary tRNA. Using flexizyme enables a desired amino acid to be bound to a tRNA having a desired anticodon so that a genetic code table can be rewritten by making an amino acid correspond to an arbitrary codon different from that of a natural genetic code.

Codon reassignment using flexizyme makes it possible to introduce an arbitrary amino acid containing a non-proteinogenic amino acid into an arbitrary position of a peptide and thereby provide a peptide having enhanced protease resistance, cellular permeability, or affinity or specificity for a target molecule.

In recent years, on the other hand, macrocyclization of peptides has attracted attentions. Macrocyclic peptides can be found in the natural world and they are known to have stable conformation. Macrocyclic peptides are known to show specificity higher than that of small non-cyclized peptides (Non-Patent Document 2) and are expected to be an inhibitor against highly difficult targets such as molecules whose protein-protein interaction or low molecular compound binding site is unknown. Restriction by a cyclic structure is thought to improve the bioavailability of peptides or their resistance against metabolism.

In such a trend toward investigation of addition of various modifications to peptides, peptides excellent in resistance against metabolism or stability in vivo and capable of penetrating a cell membrane and targeting intracellular molecules have been demanded particularly.

CITATION LIST

Non-Patent Document

Non-Patent Document 1: H. Murakami, H. Saito, and H. Suga, (2003), Chemistry & Biology, Vol. 10, 655-662.
Non-Patent Document 2: White, T. R. et al., Nature chemical biology, 7(11), 810-7.

SUMMARY

Technical Problem

An object of the present invention is to provide a peptide capable of keeping a stable structure in vivo, sufficiently excellent in resistance against metabolism, and capable of penetrating a cell membrane and reaching into cells.

Solution to Problem

The present inventors have proceeded with an investigation with a view to achieving the above-mentioned object. As a result, they have thought that a macrocyclic peptide having, in a ring portion thereof, an amino acid having at least two hydrophobic side chains has, in a hydrophilic environment, a pseudo bicyclic like structure through a noncovalent bond due to interaction between the hydrophobic side chains inside the ring, while the macrocyclic peptide can acquire affinity for a hydrophobic environment because due to a dynamic change in the structure in the hydrophobic environment, the hydrophobic group is exposed outside the molecule.

It has been confirmed that such a macrocyclic peptide synthesized actually by making use of a flexizyme developed by the present inventors has, in a hydrophilic environment, a macrocyclic structure restricted sufficiently by a hydrophobic bond and therefore can have enhanced in vivo stability.

In addition, it has been confirmed that this macrocyclic peptide penetrates a cell membrane and reaches into cells. This finding therefore suggests that as is expected, in a hydrophobic environment, a flexible pseudo bicyclic like structure not depending on a covalent bond changes dynamically and the hydrophobic side chains are exposed outside the molecule.

Further, building a library of macrocyclic peptides excellent in in vivo stability and cell membrane permeability, screening the library, and succeeding in finding an inhibitor against an intramolecular target molecule PAD4, the present inventors have completed the present invention.

Described specifically, the present invention relates to:
[1] a macrocyclic peptide having a macrocyclic structure composed of four or more amino acids,
wherein at least two amino acids of the amino acids that constitute the macrocyclic structure not adjacent to each other have a hydrophobic side chain, and
the hydrophobic side chains interact with each other in the macrocyclic structure in a hydrophobic environment;

[2] the macrocyclic peptide as described above in [1], wherein the amino acids having the hydrophobic side chain are a non-proteinogenic amino acid;

[3] the macrocyclic peptide as described above in [1] or [2], wherein the hydrophobic side chain of the amino acids is selected from the group consisting of substituted or unsubstituted, saturated or unsaturated, linear or branched alkyl groups having 4 or more carbon atoms, substituted or unsubstituted aryl groups, vinyl groups, polyoxypropylene groups, and polysiloxane groups;

[4] the macrocyclic peptide as described above in [3], wherein the hydrophobic side chain of the amino acids is a linear alkyl group having from 4 to 15 carbon atoms;

[5] the macrocyclic peptide as described above in [1] to [4], wherein the macrocyclic structure of the macrocyclic peptide has from 5 amino acids to 20 amino acids, of which two are the amino acids having a hydrophobic side chain, and the amino acids having a hydrophobic side chain are arranged substantially opposite to each other in the macrocyclic structure;

[6] the macrocyclic peptide as described above in any one of [1] to [5], having cell membrane permeability;

[7] a method of translationally synthesizing the macrocyclic peptide as described above in any one of [1] to [6], including:

a step of providing a nucleic acid that encodes the macrocyclic peptide, has codons encoding two amino acids necessary for the formation of a ring and codons encoding two amino acids having a hydrophobic side chain, and has, between two codons encoding the amino acids necessary for the formation of a ring, two codons encoding the amino acids having a hydrophobic side chain; and a step of translating the nucleic amino acid in a cell-free translation system including tRNAs aminoacylated by the two amino acids necessary for the formation of the ring and the two amino acids having a hydrophobic side chain, respectively;

[8] the method as described above in [7], wherein at least one of the tRNAs charged with the two amino acids necessary for the formation of a ring and the two amino acids having a hydrophobic side chain, respectively, is an artificial aminoacyl tRNA;

[9] the method as described above in [7] or [8], wherein the two amino acids necessary for the formation of a ring are chloroacetylated amino acid and cysteine, respectively;

[10] a screening method of the macrocyclic peptide as described above in any one of [1] to [6] having binding ability to a target molecule, including:

a step of forming a nucleic acid library including two or more nucleic acids including a nucleic acid that encodes the macrocyclic peptide, has codons encoding two amino acids necessary for the formation of a ring and codons encoding two amino acids having a hydrophobic side chain, has two codons encoding the amino acids having a hydrophobic side chain between two codons encoding the amino acids necessary for the formation of a ring, and includes a nucleic acid encoding a random amino acid sequence in a portion other than the codons encoding the amino acids necessary for the formation of a ring and the codons encoding the amino acids having a hydrophobic side chain;

a step of translating the nucleic acid library in a cell-free translation system to obtain a macrocyclic peptide library;

a step of bringing the macrocyclic peptide library into contact with a target molecule, followed by incubation; and a step of selecting a macrocyclic peptide bound to the target molecule;

[11] the nucleic acid library as described above in [10];

[12] the macrocyclic peptide library as described above in [10];

[13] a method of screening the macrocyclic peptide as described above in any one of [1] to [6] having binding ability to a target molecule including:

(a) a step of forming a library including two or more mRNAs including an mRNA that encodes the macrocyclic peptide, has codons encoding two amino acids necessary for the formation of a ring and codons encoding two amino acids having a hydrophobic side chain, has two codons encoding the amino acids having a hydrophobic side chain between two codons encoding the amino acids necessary for the formation of a ring, and encodes a random amino acid sequence in a portion other than the codons encoding the amino acids necessary for the formation of a ring and the codons encoding the amino acids having a hydrophobic side chain;

(b) a step of binding directly or indirectly puromycin to the 3' end of each of the mRNAs of the library;

(c) a step of translating the nucleic acid of the library in a cell-free translation system to obtain an mRNA-macrocyclic peptide complex library;

(d) a step of bringing the mRNA-macrocyclic peptide complex library into contact with the target molecule, followed by incubation;

(e) selecting an mRNA-macrocyclic peptide complex group bound to the target molecule, obtaining a cDNA group by a reverse transcription reaction, and amplifying the group; and (f) transcribing the cDNA group to obtain an mRNA library;

wherein the steps (a) to (f) are performed twice or more to enrich the macrocyclic peptide having binding ability to the target molecule.

Advantageous Effects of Invention

The macrocyclic peptide of the present invention forms a pseudo bicyclic like structure by the interaction between non-hydrophobic side chains of amino acids in a hydrophilic environment so that it has enhanced in vivo stability due to sufficient restriction of the macrocyclic structure. When exposed to a hydrophobic environment, on the other hand, it exhibits, as an entire molecule, hydrophobicity and can penetrate a cell membrane because the hydrophobic side chain is exposed on the molecular surface due to a dynamic change in the structure. Even when the target is an intracellular molecule, the macrocyclic peptide can produce advantages for a peptide drug such as high affinity and specificity for the target molecule and easy protein-protein interaction inhibition.

In addition, the macrocyclic peptide library and screening method according to the present invention can efficiently provide macrocyclic peptides that interact with the target molecule.

BRIEF DESCRIPTION OF DRAWINGS

FIG. 1 is a schematic view showing (A) one example of a macrocyclic peptide of the present invention, (B) an amino acid contained in the macrocyclic peptide and having an interactive hydrophobic side chain, and (C) a conformational change in a hydrophilic environment and a hydrophobic environment;

FIG. 2 shows design and construction of VB1 and VB2 mRNA libraries for expressing a peptide having a VB skeleton.

FIG. 3 is a schematic view showing a RaPID system for the selection of a VB peptide having inhibitory activity against PAD4. The VB mRNA library is transcribed from a cDNA library and is then bound to an oligonucleotide having puromycin bound at the 3' end hereof. Then, an mRNA library is translated in an FIT system from which Met has been removed and to which $^{ClAc-D}$-F-tRNAf$^{Met}_{CAU}$ and Ahep-tRNa$^{Asn-E2}_{CCA}$ have been added. Linear peptides are presented on mRNAs, respectively, followed by spontaneous cyclization through an intramolecular reaction between a sulfhydryl group of cysteine and α-carbon of an N-terminal chloroacetyl group. After reverse transcription, the peptide library is brought into contact with a target PAD4 protein. The VB peptide bound to PAD4 is recovered and the corresponding cDNA is amplified by PCR. After the above-described steps are repeated in a plurality of rounds, the sequence of the enriched mRNA is determined by cloning and sequencing.

FIG. 4 shows peptide selection in a VB1 peptide library (A) and a VB2 peptide library (B). The mRNA recovered using PAD4-immobilized magnetic beads is shown by a right bar, while the mRNA recovered only from magnetic beads binder is shown by a left bar. The sequence of clones enriched in the VB1 peptide library is shown in (C) and the sequence of clones enriched in the VB2 library is shown in (D).

FIG. 5 shows an amino acid sequence of synthesized VB1C12 and VB1C20 and a Kd value determined by SPR test.

FIG. 6 shows the results of in vitro PAD4 inhibition assay of VB peptides and Cl-amidine by the colorimetric analysis method using a COLDER solution. (A) The assay was performed by adding various concentrations of VB1 peptides to a reaction buffer containing 100 mM HEPES (pH 7.6) and 50 mM NaCl. The final concentrations of PAD4 and substrate BAEE were 0.2 μM and 10 mM, respectively. The concentration of the peptides was increased from 0 μM to 50 μM in order to measure dependence of PAD4 inhibition on the amount of VB1 peptide. (B) shows the structure of Cl-amidine known as a low molecular compound inhibitor of PAD4.

FIG. 7 shows in vitro PAD4 inhibition assay performed using VB1C12 and VB1C12-Cl-amidine warhead peptide. (A) shows the structures of VB1C12 and VB1C12-Cl-amidine analogue peptide, respectively. (B) shows the structure of Cl-amidine. (C) Assay was performed by adding various concentrations of VB1 peptide to a reaction buffer containing 100 mM HEPES (pH 7.6) and 50 mM NaCl. The final concentrations of PAD4 and substrate BAEE were 0.2 μM and 10 mM, respectively. The concentration of the peptides was increased from 0 μM to 50 μM in order to measure dependence of PAD4 inhibition on the amount of the VB1 peptide.

FIG. 8 shows the amino acid sequence of fluorescently labeled peptides obtained by chemical synthesis (Fmoc solid-phase peptide synthesis) and MALDI-TOF mass analysis results of them.

FIG. 9 shows transfer of VB1C12-Flu peptide and VB1C12-ana-Flu peptide (peptide obtained by substituting Ahep with alanine) into living HeLa cells. Only the VB1C12-Flu peptide shows fluorescence in the cells and the Ahep introduction effect was observed.

FIG. 10 shows transfer of VB1C20-Flu peptide and VB1C20-ana-Flu peptide (peptide obtained by substituting Ahep with alanine) into living HeLa cells. Only VB1C12-Flu peptide shows fluorescence in the cells and the Ahep introduction effect was observed.

FIG. 11 shows fluorescence patterns observed in living HeLa cells treated with VB1C-12-Flu and VB1C20-Flu peptides, respectively. Localization of both the peptides in respective nuclei can be confirmed.

FIG. 12 shows co-localization of a fluorescently labeled VB peptide and SYTO61 (dye for staining a nucleic acid therewith). (A) shows the results of incubating HeLa cells with 10 μM VB1C12-Flu peptide and 5 μM SYTO61 at 37° C. for 60 minutes. (B) shows the results of incubating HeLa cells with 10 μM VB1C20-Flu peptide and 5 μM SYTO61 at 37° C. for 60 minutes. Localization of both the peptides in the respective nuclei can be confirmed.

FIG. 13 shows three-dimensional scanning (Z-axis scanning) results of HeLa cells treated with 10 μM VB1C12-Flu peptide and 5 μM SYTO61 through observation using a confocal laser microscope. It shows fluorescently labeled VB1C12-flu peptide (green fluorescence) and SYTO61 (red fluorescence) in 12 continuous sections (z-stack, z-axis increment of 0.49 μm). Localization of the peptide in the nucleus can be confirmed.

DESCRIPTION OF EMBODIMENTS

[Macrocyclic Peptide]

The macrocyclic peptide of the present invention is characterized in that four or more amino acids constitute its macrocyclic structure, at least two of the amino acids not adjacent to each other have a hydrophobic side chain, and the hydrophobic side chains interact with each other inside the ring of the macrocyclic peptide in a hydrophilic environment.

The term "macrocyclic peptide" as used herein means a peptide containing a macrocyclic structure composed of four or more amino acids. The term "macrocyclic structure" as used herein means a closed-ring structure of a linear peptide intramolecularly formed by two amino acids, which are separated from each other by two or more amino acid residues, bound to each other directly, via a linker, or the like. The term "separated from each other by two or more amino acid residues" means that two amino acids have therebetween at least two amino acid residues.

The macrocyclic structure is formed by two amino acids bound to each other via a disulfide bond, a peptide bond, an alkyl bond, an alkenyl bond, an ester bond, a thioester bond, an ether bond, a thioether bond, a phosphonate ether bond, an azo bond, a C—S—C bond, a C—N—C bond, a C=N—C bond, an amide bond, a lactam bridge, a carbamoyl bond, an urea bond, a thiourea bond, an amine bond, a thioamide bond, or the like. The kind of the bond is however not limited them.

A macrocyclized peptide may have a stable peptide structure and has enhanced affinity for a target.

The number of amino acids constituting the macrocyclic structure, that is, amino acids constituting the ring of the macrocyclic peptide is not particularly limited insofar as it is 4 or more amino acids. It may be, for example, 4 or more amino acids, 5 or more amino acids, 8 or more amino acids, 15 or less amino acids, 20 or less amino acids, 25 or less amino acid, or 30 or less amino acids.

The macrocyclization may be formed not only via a bond between an N-terminal amino acid and a C-terminal amino acid of a peptide and it may be formed via a bond between a terminated amino acid and an unterminated amino acid or a bond between unterminated amino acids. When in the macrocyclic peptide, one of the amino acids to be bound for ring formation is a terminated amino acid and the other one is an unterminated amino acid, the resulting macrocyclic peptide has a macrocyclic structure with a tail-like linear peptide. Such a structure may be called hereinafter "lasso type".

In the present specification, the term "amino acid" is used in its broadest meaning and it embraces not only natural amino acids but also artificial amino acid variants and derivatives of them. The amino acids may be represented by a commonly used single-letter or three-letter code. Examples of the amino acid or derivatives thereof used herein include natural proteinogenic L-amino acids, unnatural amino acids, and chemically synthesized compounds having properties known in the art as characteristics of an amino acid. Examples of the unnatural amino acids include, but not limited to, α,α-disubstituted amino acids (such as α-methylalanine), N-alkyl-α-amino acids, D-amino acids, β-amino acids, and α-hydroxy acids, each having a main chain structure different from that of natural amino acids; amino acids (such as norleucine and homohistidine) having a side-chain structure different from that of natural amino acids; amino acids (such as "homo"amino acids, homophenylalanine, and homohistidine) having extra methylene in the side chain thereof; and amino acids (such as cysteic acid) obtained by substituting a carboxylic acid functional group in the side chain by a sulfonic acid group.

The amino acids embrace proteinogenic amino acids and non-proteinogenic amino acids.

The term "proteinogenic amino acid" as used herein means an amino acid (Arg, His, Lys, Asp, Glu, Ser, Thr, Asn, Gln, Cys, Gly, Pro, Ala, Ile, Leu, Met, Phe, Trp, Tyr, or Val) constituting a protein.

The term "non-proteinogenic amino acid" as used herein means a natural or unnatural amino acid other than the proteinogenic amino acid.

The term "amino acids not adjacent to each other" as used herein means amino acids not adjacent to each other even after a macrocycle is formed. Amino acids not adjacent to each other are amino acids separated from each other by one or more amino acid residues in a peptide.

The "hydrophobic side chains" of at least two amino acids not adjacent to each other, as used herein, may be any groups insofar as they interact with each other inside the ring of the macrocyclic peptide and stabilize the conformation. Examples include substituted or unsubstituted, saturated or unsaturated, and linear or branched alkyl groups having four or more carbon atoms (for example, 4, 5, 6, 7, 8, 9, 10, 11, 12, 13, 14, or 15 carbon atoms), substituted or unsubstituted aryl groups, a vinyl group, a polyoxypropylene group, and a polysiloxane group.

Examples of the substituent for the alkyl or aryl group include, but not limited to, halogen atoms (such as fluorine atom, chlorine atom, bromine atom, and iodine atom), a hydroxyl group, a nitro group, a cyano group, an amide group, a sulfonamide group, alkyl groups such as methyl group, ethyl group, propyl group, n-butyl group, sec-butyl group, pentyl group, hexyl group, 2-ethylhexyl group, and octyl group; alkoxy groups such as methoxy group, ethoxy group, hydroxyethoxy group, propoxy group, hydroxypropoxy group, and butoxy group; alkoxycarbonyl groups such as methoxycarbonyl group and ethoxycarbonyl group; acyl groups such as carboxyl group, formyl group, acetyl group, and benzoyl group; acyloxy groups such as acetoxy group and butyryloxy group; and aryl groups.

The macrocyclic peptide of the present invention may include an amino acid having a hydrophobic side chain that does not interact with another hydrophobic side chain. Here, in order to distinguish a hydrophobic side chain that interacts with another hydrophobic side chain from a hydrophobic side chain that does not interact with another hydrophobic side chain, the hydrophobic side chain that interacts with another hydrophobic side chain will hereinafter be called "interactive hydrophobic side chain".

An amino acid having an interactive hydrophobic side chain may be either a natural amino acid or a unnatural amino acid. As the natural amino acid, for example, leucine, isoleucine, or methionine can be used.

Examples of the unnatural amino acid include 2-aminoheptonic acid (Ahep) having, as a side chain thereof, a pentyl group and N-butoxycarbonyl-L-norleucine (Nle) having, as a side chain thereof, a butyl group.

Those skilled in the art can determine as needed the interactive hydrophobic side chain and the amino acid having an interactive hydrophobic side chain, depending on the size of the macrocyclic structure of the macrocyclic peptide or component amino acids thereof.

In the macrocyclic peptide of the present invention, at least two interactive hydrophobic side chains may be the same side chains or different side chains insofar as they interact with each other. In addition, one macrocyclic peptide typically contains two amino acids having an interactive hydrophobic side chain but it may contain three or more.

When a macrocyclic structure contains two amino acids having an interactive hydrophobic side chain, the respective positions of the amino acids are not particularly limited insofar as they interact with each other in a hydrophilic environment and the conformation of the macrocyclic structure is stabilized. For example, they may be placed substantially opposite to each other. The term "placed substantially opposite to each other" means that in the macrocyclic structure, the number of amino acid residues in two regions sandwiched by two amino acids is substantially equal. The term "the number of amino acid residues in two regions sandwiched by two amino acids is substantially equal" means that the number of amino acid residues in one of two regions is from 70% to 130% or from 80% to 120% of the number of amino acid residues in the other region.

The term "hydrophilic environment" as used herein means an environment in a high-polarity solvent such as water or various water-based buffers.

The term "hydrophobic side chains interact with each other inside the ring of a macrocyclic peptide" as used herein means that interactive hydrophobic side chains extend inward the cyclic structure of the macrocyclic peptide to form a hydrophobic bond. The interactive hydrophobic side chains form a hydrophobic bond and thereby form a pseudo bicyclic like structure inside the cyclic structure. The term "pseudo bicyclic like structure" means not a bicyclic structure via a covalent bond but means a state in which the cyclic structure of the macrocyclic peptide is in fact divided into two rings by a noncovalent bond of the hydrophobic side chains. Formation of a pseudo bicyclic like structure in a hydrophilic environment is expected to stabilize the conformation of the macrocyclic structure, improve the resistance against metabolism to enhance the in vivo stability, and at the same time, like natural macrocyclic peptides, enhance affinity or specificity for a target molecule.

In the macrocyclic peptide of the present invention, on the other hand, the bond forming the pseudo bicyclic like structure is not a covalent bond but has a flexible constitution. When it is exposed to a hydrophobic environment such as cell membrane, the structure changes dynamically and the hydrophobic side chains that interact with each other inside the ring are exposed from the molecular surface. As a result, the macrocyclic peptide molecule as a whole exhibits hydrophobicity and therefore can penetrate a cell membrane. This means that the macrocyclic peptide of the present invention is stable in vivo and at the same time, can penetrate a cell membrane and reach into cells.

When the C-terminal amino acid of the macrocyclic peptide of the present invention is not used for cyclization, this C terminal may be not limited to a carboxyl group or a carboxylate group but may be an amide or ester. The macrocyclic peptide of the present invention embraces salts thereof. Examples of the salts of the macrocyclic peptide include salts with a physiological acceptable base or acid such as inorganic acid (such as hydrochloric acid, hydrobromic acid, hydroiodic acid, sulfuric acid, or phosphoric acid) addition salts, organic acid (such as p-toluenesulfonic acid, methanesulfonic acid, oxalic acid, p-bromophenylsulfonic acid, carboxylic acid, succinic acid, citric acid, benzoic acid, or acetic acid) addition salts, inorganic bases (such as ammonium hydroxide, alkali or alkaline earth metal hydroxides, carbonates, or bicarbonates), and amino acid addition salts.

The macrocyclic peptide of the present invention may be modified through phosphorylation, methylation, acetylation, adenylylation, ADP ribosylation, glylcosylation, or the like insofar as it solves the problem of the present invention. It may be fused with another peptide or protein.

FIG. 1A shows one aspect of the macrocyclic peptide of the present invention. In this example, the macrocyclic peptide is composed of 6 amino acids and two Ahep (FIG. 1B), as unnatural amino acids, are placed at positions opposite to each other. As a result, as shown in the left and right drawings of FIG. 1C, in a hydrophilic environment, the side chains of Ahep extend inward the cyclic structure of the macrocyclic peptide and form a hydrophobic bond so that the cyclic structure is substantially divided into two rings.

As shown in the center of FIG. 1C, when the macrocyclic peptide is exposed to a hydrophobic environment such as cell membrane, the hydrophobic side chains that interact with each other inside the ring are exposed from the molecular surface and the entire molecule exhibits hydrophobicity. Due to such a constitution, the macrocyclic peptide of the present invention, when administered in vivo, may reach into cells and act on a target molecule in the cells.

[Production Process of Macrocyclic Peptide]

A preparation process of the macrocyclic peptide of the present invention is not particularly limited. The macrocyclic peptide of the present invention can be prepared by a known method or a method based on it, for example, chemical synthesis method such as liquid phase method, solid-phase method, and hybrid method using liquid phase method and solid-phase method in combination, genetic recombination method, or translational synthesis in a cell-free translation system.

1. Translational Synthesis in Cell-Free Translation System

The macrocyclic peptide of the present invention can be prepared by preparing a nucleic acid encoding it and translating the resulting nucleic acid in a cell-free translation system. The nucleic acid encoding the macrocyclic peptide can be designed as needed by those skilled in the art by using a genetic code used in vivo translation system, a reprogrammed genetic code, or a combination of them. The nucleic acid may be either DNA or RNA.

In accordance with the method using a cell-free translation system, an unnatural amino acid as well as a natural amino acid can be introduced efficiently into a peptide by using tRNA aminoacylated with an unnatural amino acid. For example, tRNA having an arbitrary anticodon can be aminoacylated with an arbitrary natural or unnatural amino acid by using artificial aminoacyl tRNA synthetase flexizyme developed by the present inventors. By using this technology, therefore, it is possible to reprogram a genetic code made of mRNA triplet so that it encodes an amino acid different from that in a vivo translation system (WO2008/059823).

For example, an initiator codon AUG encodes formylmethionine and methionine in prokaryotic cells and eukaryotic cells, respectively. When flexizyme is used, on the other hand, tRNA corresponding to an initiator codon can be aminoacylated with another amino acid so that peptide synthesis can be initiated by an arbitrary amino acid. In addition, tRNA corresponding to a codon other than the initiator codon can be aminoacylated with an arbitrary amino acid so that an arbitrary amino acid can be introduced into an arbitrary position of a peptide using a cell-free translation system.

When flexizyme is used, a hydroxy acid or carboxylic acid, as well as an amino acid, can be bound to tRNA. An arbitrary hydroxy acid or carboxylic acid can therefore also be introduced into an arbitrary position of a peptide in a cell-free translation system. The macrocyclic peptide of the present invention may therefore be prepared by introducing a hydroxy acid or carboxylic acid instead of an amino acid.

As flexizyme, for example, those described in the following documents are known:

H. Murakami, H. Saito, and H. Suga, (2003), Chemistry & Biology, Vol. 10, 655-662; H. Murakami, D. Kourouklis, and H. Suga, (2003), Chemistry & Biology, Vol. 10, 1077-1084; H. Murakami, A. Ohta, H. Ashigai, H. Suga (2006) Nature methods 3, 357-359; N. Niwa, Y. Yamagishi, H. Murakami, H. Suga, (2009) Bioorganic & Medicinal Chemistry Letters 19, 3892-3894; and WO2007/066627.

As flexizyme, original flexizyme (Fx) and altered ones thereof such as dinitrobenzyl flexizyme (dFx), enhanced flexizyme (eFx), and aminoflexizyme (aFx) are also known.

The aminoacylation method of an arbitrary tRNA with an arbitrary amino acid is not limited to a method using flexizyme and another method can also be applied to the present invention.

Non-limiting examples of unnatural amino acids that can be introduced using flexizyme are shown below. In the following table, DBE and CME are esters when these amino acids are bound to tRNA by using flexizyme and DBE represents 3,5-dinitrobenzyl ester and CME represents cyanomethyl ester.

TABLE 1

| Initiator amino acids | |
|---|---|
| Acetyl-L-alanine | DBE |
| Acetyl-L-phenylalanine | CME |
| Acetyl-L-tyrosine | CME |
| Acetyl-L-tryptophan | CME |
| Acetyl-D-alanine | DBE |
| Acetyl-D-phenylalanine | CME |
| Acetyl-D-tyrosine | CME |
| Acetyl-D-tryptophan | CME |
| N-Chloroacetyl-L-alanine | DBE |
| N-Chloroacetyl-L-phenylalanine | CME |
| N-Chloroacetyl-L-tyrosine | CME |
| N-Chloroacetyl-L-tryptophan | CME |
| N-Chloroacetyl-D-alanine | DBE |
| N-Chloroacetyl-D-phenylalanine | CME |
| N-Chloroacetyl-D-tyrosine | CME |
| N-Chloroacetyl-D-tryptophan | CME |
| N-3-chloromethylbenzoyl-L-tyrosine | CME |
| N-3-chloromethylbenzoyl-L-tryptophane | CME |

TABLE 2

| Amino acids that crosslink in peptides | |
| --- | --- |
| Nγ-(2-chloroacetyl)-α,γ-diaminobutylic acid | DBE |
| Nγ-(2-chloroacetyl)-α,γ-diaminopropanoic acid | DBE |

TABLE 3

| D-amino acid | |
| --- | --- |
| D-Serine | DBE |
| D-Phenylalanine | CME |
| D-Tyrosine | CME |
| D-Tryptophan | CME |

TABLE 4

| N-methylamino acids | |
| --- | --- |
| N-methyl-Glycine | DBE |
| N-methyl-Alanine | DBE |
| N-methyl-Serine | DBE |
| N-methyl-Histidine | DBE |
| N-methyl-Phenylalanine | CME |
| N-methyl-Tyrosine | CME |
| N-methyl-Tryptophan | CME |

TABLE 5

| Peptoid blocks | |
| --- | --- |
| N-ethyl-Glycine | DBE |
| N-n-propyl-Glycine | DBE |
| N-n-butyl-Glycine | DBE |
| N-n-pentyl-Glycine | DBE |
| N-n-hexyl-Glycine | DBE |
| N-n-heptyl-Glycine | DBE |
| N-n-octyl-Glycine | DBE |
| N-isopentyl-Glycine | DBE |
| N-(2-phenylethyl)-Glycine | CME |
| N-(3-phenylpropyl)-Glycine | CME |
| N-[2-(p-hydroxyphenyl)ethyl]-Glycine | CME |

TABLE 6

| Other special amino acids | |
| --- | --- |
| p-biphenylalanine | CME |
| p-trifluoromethylphenylalanine | CME |
| p-acidophenylalanine | CME |
| p-biotinyl-aminophenylalanine | CME |
| e-N-Biotinyl-lysine | DBE |
| e-N-Acetyl-lysine | DBE |
| L-Citrulline | DBE |
| L-5-Hydroxytryptophan | CME |
| L-1,2,3,4-Tetrahydroisoquinoline-3-carboxylic acid | DBE |
| Aminoisobutyric acid | DBE |
| N-methyl-aminoisobutyric acid | DBE |
| N-methyl-Phenylgycine | CME |

The above-mentioned unnatural amino acids can be used as an amino acid of the macrocyclic peptide of the present invention having an interactive hydrophobic side chain insofar as they have a side chain having hydrophobic interaction. Preferred examples of the amino acid having an interactive hydrophobic side chain listed in the above table include, but not limited to N-n-butyl-Glycine, N-n-pentyl-Glycine, N-n-hexyl-Glycine, N-n-heptyl-Glycin, N-n-octyl-Glycine, and N-isopentyl-Glycine.

The "cell-free translation system" used herein is also called "cell-free protein synthesis system". It is a translation system not using cells such as Escherichia coli as are but making use of a component present in cells such as Escherichia coli. This system includes a system using mainly a cell extract and a system using a reaction liquid (re-constituted cell-free translation system) reconstituted of purified components of a cell extract. By the cell-free translation system, a high-purity target product can be obtained without purifying an expression product.

Examples of the system using mainly a cell extract include systems using an Escherichia coli extract, a wheat germ extract, a rabbit reticulocyte extract, and an insect cell extract.

The reconstituted cell-free translation system can be constructed of a ribosome protein, aminoacyl tRNA synthetase (ARS), ribosomal RNA, amino acid, rRNA, GTP, ATP, translation initiation factor (IF), elongation factor (EF), termination factor (RF), and ribosome regeneration factor, another factor necessary for translation, and the like, each of which has been purified.

Energy may be supplied continuously to these translation systems by dialysis. RNA polymerase may be added them for carrying out transcription from DNA.

Examples of a commercially available cell-free translation system include Escherichia-coli derived systems such as RTS-100 (registered trade mark) of Roche Diagnostics, systems using a wheat germ extract such as those of ZOE-GENE Corporation or CellFree Sciences, and reconstituted translation systems such as PURESYSTEM (registered trade mark) of PGI and PURExpress (registered trade mark) In Vitro Protein Synthesis Kit of New England Biolabs.

As a system using a ribosome of Escherichia coli, for example, technologies described in the following documents are known. They may be used.

H. F. Kung et al., 1997. The Journal of Biological Chemistry Vol. 252, No. 19, 6889-6894; M. C. Gonza et al., 1985, Proceeding of National Academy of Sciences of the United States of America Vol. 82, 1648-1652; M. Y. Pavlov and M. Ehrenberg, 1996, Archives of Biochemistry and Biophysics Vol. 328, No. 1, 9-16; Y. Shimizu et al., 2001, Nature Biotechnology Vol. 19, No. 8, 751-755; H. Ohashi et al., 2007, Biochemical and Biophysical Research Communications Vol. 352, No. 1, 270-276.

When the reconstituted translation system is used, constituting components of the translation system can be selected freely, depending on the using purpose. Reconstitution of a translation system not containing a specific amino acid or a translation system not containing aminoacyl tRNA corresponding to a specific amino acid and therefore incapable of producing the aminoacyl tRNA causes absence of tRNA that decodes a codon corresponding to the amino acid. By aminoacylating a tRNA having an anticodon corresponding to the codon with a desired amino acid by using a flexizyme and then adding the resulting aminoacylated tRNA to a translation system, the desired amino acid can be introduced into a peptide with an aid of the codon.

A FIT system used in Example which will be described later is one example of re-constituted translation systems for efficient reprogramming of a genetic code developed by the present inventors.

By making use of the above-mentioned technology, an amino acid necessary for the formation of a ring or an amino acid having hydrophobic side chains can be introduced into a desired position of the macrocyclic peptide of the present invention.

In this case, codons that encode two amino acids (which may hereinafter be called "ring-forming amino acids) necessary for ring formation and codons that encode two amino acids having an interactive hydrophobic side chain are introduced into a nucleic acid that encodes the macrocyclic peptide. A nucleic acid sequence can be determined so that it has, from the 5' end, a codon encoding a ring forming amino acid, a codon encoding an amino acid having a hydrophobic side chain, a codon encoding an amino acid having a hydrophobic side chain, and a codon encoding a ring forming amino acid are arranged in order of mention and the appropriate number of amino acids are inserted between them.

For example, when tRNA$^{Asn\text{-}E2}{}_{CCA}$ which is originally a tRNA corresponding to Asn is aminoacylated with an unnatural amino acid having a hydrophobic side chain and added to a re-constituted translation system and Asn is removed from the translation system, the unnatural amino acid having a hydrophobic side chain is introduced into the position of a CCA codon instead of Asn. Introduction of a CCA codon in advance into a position of a nucleic acid encoding the macrocyclic peptide at which an unnatural amino acid having a hydrophobic side chain is to be introduced makes it possible to introduce an amino acid having two hydrophobic side chains into a position most suited for interaction and formation of a pseudo bicyclic like structure.

Although a method of macrocyclizing a peptide is not particularly limited, a translationally synthesized peptide can be macrocyclized spontaneously by incorporating, for example, an amino acid having the functional group 1 shown below and an amino acid having a functional group 2 corresponding thereto. Either the functional group 1 or 2 may be placed on the N-terminal side; they may be placed at the N-terminal and C-terminal; one of them may be a terminal amino acid and the other one may be a non-terminal amino acid; or both may be non-terminal amino acids.

TABLE 7

|     | Functional group 1 | Functional group 2 |
| --- | --- | --- |
| (A) | —C(=O)—CH$_2$—X$_1$ (A-1) | HS— (A-2) |
| (B) | —C≡C—H (B-1) | N$_3$— (B-2) |
| (C) | —Ar—CH$_2$NH$_2$ (C-1) | HO-(5-hydroxyindole) (C-2) |
| (D) | —C=C—CH$_2$—X$_1$ (D-1) | HS— (D-2) |
| (E) | —Ar—CH$_2$—X$_1$ (E-1) | HS— (E-2) |

In the above formulas, X$_1$ represents Cl, Br, or I and Ar represents a substituted or unsubstituted aromatic ring.

As the amino acid having a functional group of (A-1), for example, a chloroacetylated amino acid can be used. Examples of the chloroacetylated amino acid include N-chloroacetyl-L-alanine, N-chloroacetyl-L-phenylalanine, N-chloroacetyl-L-tyrosine, N-chloroacetyl-L-tryptophan, N-3-(2-chloroacetamido)benzoyl-L-phenylalanine, N-3-(2-chloroacetamido)benzoyl-L-tyrosine, N-3-(2-chloroacetamido)benzoyl-L-tryptophane, β-N-chloroacetyl-L-diaminopropanoic acid, γ-N-chloroacetyl-L-diaminobutyric acid, σ-N-chloroacetyl-L-ornithine, and ε-N-chloroacetyl-L-lysine, and D-amino acid derivatives corresponding thereto.

Examples of amino acids having the functional group (A-2) include cysteine, homocysteine, mercaptonorvaline, mercaptonorleucine, 2-amino-7-mercaptoheptanoic acid, 2-amino-8-mercaptooctanoic acid, amino acids obtained by protecting the SH group of these amino acids and then eliminating the protecting group, and D-amino acid derivatives corresponding thereto.

The cyclization method may be carried out according to the method described, for example, in Kawakami, T. et al., Nature Chemical Biology 5, 888-890 (2009); Yamagishi, Y. et al., ChemBioChem 10, 1469-1472 (2009); Sako, Y. et al., Journal of American Chemical Society 130, 7932-7934 (2008); Goto, Y. et al., ACS Chemical Biology 3, 120-129 (2008); and Kawakami T. et al, Chemistry & Biology 15, 32-42 (2008), and WO2008/117833.

As amino acids having the functional group (B-1), for example, propargylglycine, homopropargylglycine, 2-amino-6-heptynoic acid, 2-amino-7-octynoic acid, and 2-amino-8-nonynoic acid can be used. In addition, 4-pentynoylated or 5-hexynoylated amino acids can also be used. Examples of the 4-pentynoylated amino acids include N-(4-pentenoyl)-L-alanine, N-(4-pentenoyl)-L-phenylalanine, N-(4-pentenoyl)-L-tyrosine, N-(4-pentenoyl)-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophane, β-N-(4-pentenoyl)-L-diaminopropanoic acid, γ-N-(4-pentenoyl)-L-diaminobutyric acid, σ-N-(4-pentenoyl)-L-ornithine, and ε-N-(4-pentenoyl)-L-lysine, and D-amino acid derivatives corresponding thereto.

As amino acids having the functional group (B-2), for example, azidoalanine, 2-amino-4-azidobutanoic acid, azidoptonorvaline, azidonorleucine, 2-amino-7-azidoheptanoic acid, and 2-amino-8-azidooctanoic acid can be used. In addition, azidoacetylated or 3-azidopentanoylated amino acids can also be used. Examples of the azidoacetylated amino acids include N-azidoacetyl-L-alanine, N-azidoacetyl-L-phenylalanine, N-azidoacetyl-L-tyrosine, N-azidoacetyl-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophane, β-N-azidoacetyl-L-diaminopropanoic acid, γ-N-azidoacetyl-L-diaminobutyric acid, σ-N-azidoacetyl-L-ornithine, and ε-N-azidoacetyl-L-lysine, and D-amino acid derivatives corresponding thereto.

The cyclization method can be performed according to the method described, for example, in Sako, Y. et al., Journal of American Chemical Society 130, 7932-7934 (2008) or WO2008/117833.

Examples of amino acids having the functional group (C-1) include N-(4-aminomethyl-benzoyl)-phenylalanine ($_{AMB}$F) and 4-3-aminomethyltyrosine.

Examples of amino acids having the functional group (C-2) include 5-hydroxytryptophan (W$_{oH}$).

The cyclization method can be performed according to the method described, for example, in Yamagishi, Y. et al., ChemBioChem 10, 1469-1472 (2009) or WO2008/117833.

Examples of amino acids having the functional group (D-1) include 2-amino-6-chloro-hexynoic acid, 2-amino-7-chloro-heptynoic acid, and 2-amino-8-chloro-octynoic acid.

Examples of amino acids having the functional group (D-2) include cysteine, homocysteine, mercaptonorvaline, mercaptonorleucine, 2-amino-7-mercaptoheptanoic acid, and 2-amino-8-mercaptooctanoic acid, amino acids obtained by protecting the SH group of these amino acids and then eliminating the protecting group, and D-amino acid derivatives corresponding thereto.

The cyclization method can be performed according to the method described, for example, in WO2012/074129.

Examples of the amino acid (E-1) include N-3-chloromethylbenzoyl-L-phenylalanine, N-3-chloromethylbenzoyl-L-tyrosine, and N-3-chloromethylbenzoyl-L-tryptophane.

Examples of the amino acid (E-2) include cysteine, homocysteine, mercaptonorvaline, mercaptonorleucine, 2-amino-7-mercaptoheptanoic acid, and 2-amino-8-mercaptooctanoic acid, and amino acids obtained by protecting the SH group of these amino acids and then eliminating the protecting group, and D-amino acid derivatives corresponding thereto.

2. Synthesis by Solid-Phase Method

The macrocyclic peptide of the present invention can be prepared also by solid-phase synthesis.

In solid-phase method, esterification is performed, for example, between the hydroxyl group of a hydroxyl-containing resin and the carboxyl group of a first amino acid (usually, C-terminal amino acid of a target peptide) having an α-amino group protected with a protecting group. As the esterifying catalyst, usable is a known dehydration condensation agent such as 1-mesitylenesulfonyl-3-nitro-1,2,4-triazole (MSNT), dicyclohexylcarbodiimide (DCC), and diisopropylcarbodiimide (DIPCDI).

Next, the protecting group of the α-amino group of the first amino acid is eliminated and at the same time, a second amino acid having all the functional groups protected except the main chain carboxyl group is added to activate the carboxyl group and bind the first and second amino acids to each other. Then, the α-amino group of the second amino acid is deprotected and a third amino acid having all the functional groups protected except the main chain carboxyl group is added to activate the carboxyl group and bind the second and third amino acids to each other. The above-described reactions are repeated to synthesize a peptide having an intended length. Then, all the functional groups are deprotected.

Examples of the resin for solid-phase synthesis include Merrifield resin, MBHA resin, Cl-Trt resin, SASRIN resin, Wang resin, Rink amide resin, HMFS resin, Amino-PEGA resin (Merck), and HMPA-PEGA resin (Merck). These resins may be provided for use after washed with a solvent (dimethylformamide (DMF), 2-propanol, methylene chloride, or the like).

Examples of the protecting group of the α-amino acid include a benzyloxycarbonyl (Cbz or Z) group, a tert-butoxycarbonyl (Boc) group, a fluorenylmethoxycarbonyl (Fmoc) group, a benzyl group, an allyl group, and an allyloxycarbonyl (Alloc) group. The Cbz group can be removed using hydrofluoric acid, hydrogenation, or the like; the Boc group can be removed using trifluoroacetic acid (TFA); and the Fmoc group can be removed by the treatment with piperidine.

For protection of the α-carboxyl group, usable are a methyl ester, an ethyl ester, a benzyl ester, a tert-butyl ester, cyclohexyl ester, or the like.

As other functional groups of an amino acid, the hydroxyl group of serine or threonine can be protected with a benzyl group or a tert-butyl group and the hydroxyl group of tyrosine can be protected with a 2-bromobenzyloxycarbonyl group or a tert-buty group. The amino group of a lysine side chain or the carboxyl group of glutamic acid or aspartic acid can be protected in a manner similar to that used for protecting the α-amino group or α-carboxyl group.

The carboxyl group can be activated with a condensing agent. Examples of the condensing agent include dicyclohexylcarbodiimide (DCC), diisopropylcarbodiimide (DIPCDI), 1-ethyl-3-(3-dimethylaminopropyl)carbodiimide (EDC or WSC), (1H-benzotriazol-1-yloxy)tris(dimethylamino)phosphonium hexafluorophosphate (BOP), and 1-[bis(dimethylamino)methyl]-1 H-benzotriazolium-3-oxide hexafluorophosphate (HBTU).

A peptide chain can be cleaved from the resin can be achieved by treating it with an acid such as TFA or hydrogen fluoride (HF).

[Macrocyclic Peptide Library and Screening Method]

The present invention also provides a library of the above-described macrocyclic peptide and a screening method using the library.

The term "macrocyclic peptide library" as used herein means a combination of peptides including a plurality of macrocyclic peptides including, as a portion thereof other than a ring forming amino acid and an amino acid having a hydrophobic side chain, a random amino acid sequence.

All the amino acids other than the ring forming amino acid and amino acid having a hydrophobic side chain may have a random sequence or some of them may have a random sequence.

Such a library can be obtained by providing a plurality of nucleic acids that encode a macrocyclic peptide and contain, in a portion thereof other than a codon encoding a ring forming amino acid and a codon encoding an amino acid having a hydrophobic side chain, a nucleic acid encoding a random amino acid sequence and translating them in a cell-free translation system.

The nucleic acid encoding a random amino acid sequence is represented by, for example, (NNT)x, wherein N represents A, T, G or C and x is an arbitrary integer and can be selected depending on the number of amino acids of the random amino acid sequence. A nucleic acid encoding an intended macrocyclic peptide library can be prepared by placing, as needed, (NNT)x, the codon encoding a ring forming amino acid, and the codon encoding an amino acid having a hydrophobic side chain. As one example, the nucleic acid encoding the macrocyclic peptide of the present invention may contain the following sequence:

(SEQ ID NO: 1)
AUG-(NNU)$_{2-3}$-AUG-(NNU)$_{5-7}$-AUG-(NNU)$_{2-3}$-UGU-GGC (SEQ ID NO: 2)
AUG-(NNU)$_{2-4}$-AUG-(NNU)$_{5-7}$AUG-UGU-GGC

The terminal AUG codons are assigned to the ring forming amino acid that binds to cysteine encoded by UGU and other AUG codons are assigned to the amino acid having a hydrophobic side chain. Repeated NNUs are translated into a random amino acid sequence. The peptide thus translated forms a macrocyclic structure by spontaneous reaction.

In preparing the macrocyclic peptide library, several kinds of nucleic acids encoding it may be mixed. This enhances diversity of the library and increases possibility of obtaining peptides having activity on the target molecule.

The screening method using the macrocyclic peptide library includes a step of bringing the macrocyclic peptide library into contact with a target molecule and then incubating the resulting mixture.

The target substance is not particularly limited herein and may be, for example, a low molecular compound, a high molecular compound, a nucleic acid, a peptide, a protein, sugar, or a lipid. Typically, it is a protein.

In particular, the macrocyclic peptide of the present invention has high in vivo stability and excellent cell membrane permeability so that an intracellular protein can also be used as a target. The macrocyclic peptide of the present invention is also excellent in protease resistance so that screening can also be performed with a target molecule having protease activity.

The target substance can be brought into contact with the macrocyclic peptide library, for example, while immobilizing it onto a solid-phase support. The "solid-phase support" as used herein is not particularly limited insofar as it is a support onto which the target substance can be immobilized. Examples include microtiter plates, substrates, and beads made of glass, a metal, a resin, or the like, nitrocellulose membranes, nylon membranes, and PVDF membranes. The target substance can be immobilized onto such a solid-phase support in a known manner.

The target substance and the library are brought into contact with each other in a buffer selected as needed and they are interacted with while controlling pH, temperature, time, and the like.

The screening method of the present invention further includes a step of selecting a macrocyclic peptide that has bound to the target substance. With regard to binding to the target substance, a peptide is detectably labeled by a known method in advance and after the above-described incubation, the surface of the solid-phase support is washed with a buffer, and then a compound that has bound to the target substance is detected.

Examples of the detectable label include enzymes such as peroxidase and alkaline phosphatase, radioisotopes such as $^{125}I$, $^{131}I$, $^{35}S$, and $^{3}H$, fluorescent substances such as fluorescein isothiocyanate, rhodamine, dansyl chloride, phycoerythrin, tetramethyl rhodamine isothiocyanate, and near infrared fluorescent materials, light-emitting substances such as luciferase, luciferin, and aequorin, and nanoparticles such as gold colloid and quantum dot. When an enzyme is used as the label, the compound can be detected by adding a substrate of the enzyme to develop a color. The compound can also be detected by binding biotin to a peptide and then binding avidin or streptavidin labeled with an enzyme or the like to the biotin-bound peptide.

The above-described step can not only detect or analyze the presence/absence or degree of binding but also analyze the enhanced or inhibited activity of the target substance and thereby identify a macrocyclic peptide having such enhanced or inhibited activity. By such a method, a macrocyclic peptide having physiological activity and useful as a drug can be obtained.

Screening can also be performed by applying the macrocyclic peptide library to an mRNA display method. This mRNA display method is a method of binding, in translating an mRNA, the mRNA to a synthesized peptide in some manner to associate a phenotype (peptide) and a nucleic acid sequence (mRNA) with each other.

As a method of binding the mRNA to the synthesized peptide, widely used is a method of binding puromycin to the 3' end of the mRNA directly or via a linker.

Application of the macrocyclic peptide library to the mRNA display method is performed by preparing an mRNA library encoding the macrocyclic peptide library and then binding puromycin to the 3' end of each of the mRNAs. Although a binding method is not particularly limited, for example, a method of binding a linker composed of a DNA complementary to the 3' end of the mRNA to puromycin in advance and then hybridizing between this DNA and mRNA can be used.

An mRNA-peptide complex library can be obtained by translating the puromycin-bound mRNA library in a cell-free translation system. A peptide portion is spontaneously cyclized into an mRNA-macrocyclic peptide library.

Then, the mRNA-macrocyclic peptide library brought into contact with a target molecule is incubated and the mRNA-macrocyclic peptide complex group bound to the target molecule is selected. This step can be carried out, for example, by immobilizing the target molecule to a solid-phase surface and selecting an mRNA-macrocyclic peptide complex trapped on the solid-phase surface.

Reverse transcription of the resulting mRNA-macrocyclic peptide complex group is performed to obtain a cDNA group. This cDNA encodes a macrocyclic peptide that binds to the target molecule.

An mRNA library can be obtained again by amplifying the cDNA group and transcribing it. In this mRNA library, compared with the mRNA library obtained first, the molecule that binds to the target molecule has a higher concentration. By performing a plurality of times of the above-described step, the molecule that binds to the target molecule can be enriched gradually.

The amino acid sequence of the enriched macrocyclic peptide can be identified by analyzing the cDNA sequence so that a macrocyclic peptide having high affinity for the target molecule can be produced based on the sequence data.

The macrocyclic peptide which is obtained by screening the macrocyclic peptide library of the present invention and binds to the target molecule may then be optimized by adding modification using a known method or a method based thereon.

A RaPID system (Yamagishi, Y. et al., Chemistry & biology, 2011, 18(12), 1562-70) used in Example which will be described later is one example of a screening system using a FIT system and mRNA display in combination. Screening using a peptide library including nonproteins can be achieved by this RaPID system which is an integration of a reprogramming technology of a genetic code using the FIT system with the mRNA display method. The present inventors have previously succeeded in discovery of a kinase inhibitor (Hayashi, Y. et al., 2012, ACS chemical biology, 7(3), 607-13.) and histone deacetylase (SIRT2) inhibitor (Morimoto, J., et al., 2012, Angewandte Chemie (International et. In English), 51(14), 3423-7) from a non-standard cyclic peptide library by using this RaPID system. The peptide inhibitors thus discovered show markedly high selectivity to isoforms other than kinase and histone deacetylase. Thus, the RaPID system is a technology useful for screening of a non-standard peptide library excellent in diversity.

[Peptidyl Arginine Deaminase 4 (PAD4) Inhibitor]

As shown in Example, the present inventors identified an inhibitor against a PAD4 protein by using the macrocyclic peptide library of the present invention. The present invention also embraces a macrocyclic peptide serving as a PAD4 inhibitor.

PAD4 is a protein functioning as histone deaminase that converts methyl arginine into citrulline by a reaction contrary to methylation of arginine. It has already been found that a protein containing citrulline is produced by post-translational modification of an arginine residue by PAD4. PAD4 is thought to be involved in apoptosis, formation of neutrophil extracellular traps, functional change of chemokine, and control of DNA transcription. PAD4 is also strongly involved in onset of articular rheumatism (Firestein, G. S. (2003) Nature, 423(6937), 356-61.). PAD4 has therefore attracted attentions widely as a therapeutic target and a PAD4 specific inhibitor has been required urgently. It has been reported that a low molecular compound Cl-amidine is a PAD4 inhibitor. It has however a micromolar level $IC_{50}$ and insufficient selectivity to different isoforms of PAD enzymes. There is therefore a demand for a new PAD4 selective inhibitor having higher specificity.

The amino acid sequence of a macrocyclic peptide which may serve as a PAD4 inhibitor is represented by the following formula (I):

$$(Xaa_1)m-Xaa_2-(Xaa_3)n-Xaa_4-(Xaa_5)o \quad (I)$$

In the above formula, m stands for an integer from 1 to 5, n stands for an integer from 4 to 8, and o stands for an integer from 1 to 5.

In the above formula, m pieces of $Xaa_1$, n pieces of $Xaa_3$, o pieces of $Xaa_5$ each represents an amino acid selected independently, and $Xaa_2$ and $Xaa_4$ each represent an amino acid having an interactive hydrophobic side chain. One amino acid of m pieces of $Xaa_1$ and one amino acid of o pieces of $Xaa_5$ intramolecularly bind to each other to form a macrocycle. For example, one amino acid of m pieces of $Xaa_1$ may be used as an amino acid having the above-mentioned functional group 1 and one amino acid of o pieces of $Xaa_5$ may be used as an amino acid having the functional group 2; or one amino acid of m pieces of $Xaa_1$ may be used as an amino acid having the above-mentioned functional group 2 and one amino acid of o pieces of $Xaa_5$ may be used as an amino acid having the functional group 1.

The following are specific examples of the peptide represented by the formula (1):

VB1C12:
(SEQ ID NO: 3)
$^{ClAc-D}$-F-N-A-Ahep-Y-P-Y-R-P-P-Ahep-T-S-C

VB1C20:
(SEQ ID NO: 4)
$^{ClAc-D}$-F-D-A-Ahep-Y-P-F-R-P-P-Ahep-A-H-C

VB1C21:
(SEQ ID NO: 5)
$^{ClAc-D}$-F-Y-R-C-Ahep-H-P-V-P-V-Ahep-P-T-P-C

VB1C25:
(SEQ ID NO: 6)
$^{ClAc-D}$-F-N-A-Ahep-Y-P-F-R-P-P-Ahep-T-T-C

VB1C35:
(SEQ ID NO: 7)
$^{ClAc-D}$-F-Y-R-C-Ahep-Y-P-V-P-R-Ahep-T-R-P-C

VB1C36:
(SEQ ID NO: 8)
$^{ClAc-D}$-F-Y-R-C-Ahep-Y-P-L-P-S-P-P-Ahep-T-P-H-C

VB2C15:
(SEQ ID NO: 9))
$^{ClAc-D}$-F-Y-R-C-Ahep-Y-P-I-P-R-P-P-Ahep-C

VB2C35:
(SEQ ID NO: 10)
$^{ClAc-D}$-F-Y-R-C-Ahep-N-P-I-P-A-L-P-Ahep-C

VB2C37:
(SEQ ID NO: 11)
$^{ClAc-D}$-F-Y-R-C-Ahep-H-P-V-P-R-P-P-Ahep-C

VB2C11:
(SEQ ID NO: 12)
$^{ClAc-D}$-F-V-S-R-S-Ahep-F-D-A-L-P-N-N-Ahep-C

VB2C28:
(SEQ ID NO: 13)
$^{ClAc-D}$-F-P-S-I-R-Ahep-A-F-P-H-T-N-P-Ahep-C

Macrocyclic peptides having an amino acid sequence obtained by adding, substituting, or deleting one or more amino acids from the above amino acid sequences and having a PAD4 inhibitory effect are also embraced in the PAD4 inhibitor of the present invention.

Macrocyclic peptides having an amino acid sequence having 70% or more, 80% or more, 90% or more, 95% or more, or 98% or more sequence homology with the above amino acid sequences and having a PAD4 inhibitory effect are also embraced in the PAD4 inhibitor of the present invention.

Similar to the macrocyclic peptide of the present invention, the PAD4 inhibitor peptides can be prepared by various processes. They may be modified through phosphorylation, methylation, acetylation, adenylylation, ADP ribosylation, glylcosylation, or the like, depending on the using purpose. The PAD4 inhibitor peptides may be salts with a physiologically acceptable base or acid.

These peptides may be used for drug compositions for treating diseases in which the PAD4 inhibitor is involved.

The administration route of the drug composition is not particularly limited and it may be administered either orally or parenterally. Examples of the parenteral administration include administration by injection such as intramuscular, intravenous, or subcutaneous injection, transdermal administration, and transmucosal administration (nasal, buccal, ocular, pulmonary, vaginal, or rectal).

Since the peptide in the drug composition is likely to be metabolized and excreted, it can be subjected to various modifications. For example, a polypeptide can have longer residence time in blood and reduced antigenicity by adding thereto polyethylene glycol (PEG) or sugar chain. A polypeptide may be included in an emulsion, nanoparticles, nanospheres, or the like used as a sustained-release base and prepared using a biodegradable polymer compound such as polylactic acid glycol (PLGA), porous hydroxyapatite, liposome, surface-modified liposome, or unsaturated fatty acid. When it is administered transdermally, it can be penetrated through the stratum corneum by passing a weak electrical current through the skin surface (iontophoresis)

With regard to the drug composition, the effective ingredient thereof may be used as is or a preparation obtained by adding thereto a pharmaceutically acceptable carrier, excipient, additive, or the like may be used. Examples of the dosage form include liquids and solutions (for example, injections), dispersions, suspensions, tablets, pills, powders, suppositories, powders, fine granules, granules, capsules, syrups, troches, inhalants, ointments, ophthalmic preparations, nasal preparations, ear preparations, and cataplasms.

The preparation can be obtained in a conventional manner by using, for example, an excipient, a binder, a disintegrant, a lubricant, a dissolving agent, a solubilizing agent, a colorant, a taste/odor corrigent, a stabilizer, an emulsifier, an absorption promoter, a surfactant, a pH regulator, an antiseptic, or an antioxidant as needed.

Examples of the ingredient to be used for obtaining the preparation include, but not limited to, purified water, saline, phosphate buffer, pharmaceutically acceptable organic solvents such as dextrose, glycerol, and ethanol, animal or vegetable oils, lactose, mannitol, glucose, sorbitol, crystalline cellulose, hydroxypropyl cellulose, starch, corn starch, silicic anhydride, magnesium aluminum silicate, collagen, polyvinyl alcohol, polyvinyl pyrrolidine, carboxyvinyl polymer, carboxymethylcellulose sodium, sodium polyacrylate, sodium alginate, water-soluble dextran, carboxymethyl starch sodium, pectin, methyl cellulose, ethyl cellulose, xanthan gum, gum arabic, tragacanth, casein, agar, polyethylene glycol, diglycerin, glycerin, propylene glycol, petrolatum, paraffin, octyl dodecyl myristate, isopropyl myristate, higher alcohol, stearyl alcohol, stearic acid, and human serum albumin.

Usable examples of the absorption promoter for improving absorption of a poorly absorbable drug having difficulty in transmucosal absorption of peptides include surfactants such as polyoxyethylene lauryl ethers, sodium lauryl sulfate, and saponin; bile salts such as glycolate, deoxycholate, and taurocholate; chelating agents such as EDTA and salicylic acid; fatty acids such as caproic acid, capric acid, lauric acid, oleic acid, linoleic acid, and mixed micelle; enamine derivatives, N-acylcollagen peptide, N-acylamino acid, cyclodextrins, chitosans, and nitric oxide donors.

Pills or tablets may also be sugar, gastric, or enteric coated.

Injections may contain distilled water for injection, physiological saline, propylene glycol, polyethylene glycol, a vegetable oil, an alcohol, or the like. It may further contain a humectant, an emulsifier, a dispersant, a stabilizer, a dissolving agent, a solubilizing agent, an antiseptic, or the like.

The complete disclosure of the patent documents and non-patent documents cited herein is incorporated herein by reference in their entirety.

EXAMPLES

The present invention will hereinafter be described specifically based on examples. The present invention is not limited to or by them. Those skilled in the art can change the present invention into various aspects without departing from the meaning of the present invention and such a change is also embraced within the scope of the present invention.

A. Design and Construction of mRNA Library for Expression of the Macrocyclic Peptide of the Present Invention 1. Material and Method 1-1. Compounds All the compounds and reagents were purchased from Watanabe Chemical Industries, Nacalai Tesque, Tokyo Chemical Industry, or Sigma-Aldrich Japan. The compounds thus purchased were used without further purification unless otherwise particularly stated herein and as a buffer, water treated with Sartorius Filtration System (18.2 MΩ)) was used.

1-2. Oligonucleotide Primer

The following are oligonucleotide primers used. They were all purchased from Operon Biotechnologies (Japan). T1-T5 was used for preparation of tRNA.

P1:
(SEQ ID NO: 14)
5'-GTAATACGACTCACTATAGGCGGGGTGGAGCAGCCTGGTAGCTCGT CGG-3'

P2:
(SEQ ID NO: 15)
5'-GAACCGACGATCTTCGGGTTATGAGCCCGACGAGCTACCAGCCT-3'

P3:
(SEQ ID NO: 16)
5'-GGCGTAATACGACTCACTATAG-3'

P4:
(SEQ ID NO: 17)
5'-TGGTTGCGGGGGCCGGATTTGAACCGACGATCTTCGGG-3'

P5:
(SEQ ID NO: 18)
5'-TGGTTGCGGGGGCCCGATTT-3'

P6:
(SEQ ID NO: 19)
5'-GTAATACGACTCACTATAGGCTCTGTAGTTCAGTCGGTAGAACGGC GGA-3'

P7:
(SEQ ID NO: 20)
5'-GAACCAGTGACATACGGATTATGAGTCCGCCGTTCTACCGACT-3'

P8:
(SEQ ID NO: 21)
5'-TGGCGGCTCTGACTGGACTCGAACCAGTGACATACGGA-3'

P9:
(SEQ ID NO: 22)
5'-TGGCGGCTCTGACTGGACTC-3'

P10:
(SEQ ID NO: 23)
5'-GTAATACGACTCACTATAGGATCGAAAGATTTCCGC-3'

P11:
(SEQ ID NO: 24)
5'-ACCTAACGCTAATCCCCTTTCGGGGCCGCGGAAATCTTTCGATCC-3'

P12:
(SEQ ID NO: 25)
5'-ACCTAACGCTAATCCCCT-3'

P13:
(SEQ ID NO: 26)
5'-GAACCAGTGACATACGGATTGGAGTCCGCCGTTCTACCGACT-3'

M1:
(SEQ ID NO: 27)
5'-TAATACGACTCACTATAGGGTTAACTTTAACAAGGAGAAAAACAT G-3'

M2:
(SEQ ID NO: 28)
5'-AATCGGCGGAATAGACTTGGTCATCATGTTTTTCTCCTTGTTAAA GT-3'

M3:
(SEQ ID NO: 29)
5'-GGCGTAATACGACTCACTATAG-3'

M4:
(SEQ ID NO: 30)
5'-CGTCGTCCTTGTAGTCACAGTCCGGAAACATAATCGGCGGAATAG ACTT-3'

M5:
(SEQ ID NO: 31)
5'-TTACTTGTCGTCGTCGTCCTTGTAGTCAC-3'

VF:
(SEQ ID NO: 32)
5'-TAATACGACTCACTATAGGGTTGAACTTTAAGTAGGAGATATATC CATG-3'

VR:
(SEQ ID NO: 33)
5'-TTTCCGCCCCCCGTCCTAAGACCCAGACCCAGACCCACA-3'

VB1-1:
(SEQ ID NO: 34)
5'-AGACCCAGACCCAGACCCACAANNANNCATANNANNANNANNANNC
ATANNANNCATGGATATATCTCCTACTTAAAG-3'

VB1-2:
(SEQ ID NO: 35)
5'-AGACCCAGACCCAGACCCACAANNANNCATANNANNANNANNANNA
NNCATANNANNCATGGATATATCTCCTACTTAAAG-3'

VB1-3:
(SEQ ID NO: 36)
5'-AGACCCAGACCCAGACCCACAANNANNCATANNANNANNANNNNAN
NANNCATANNANNCATGGATATATCTCCTACTTAAAG-3'

VB1-4:
(SEQ ID NO: 37)
5'-AGACCCAGACCCAGACCCACAANNANNANNCATANNANNANNANNA
NNCATANNANNCATGGATATATCTCCTACTTAAAG-3'

VB1-5:
(SEQ ID NO: 38)
5'-AGACCCAGACCCAGACCCACAANNANNANNCATANNANNANNANNA
NNANNCATANNANNCATGGATATATCTCCTACTTAAAG-3'

VB1-6:
(SEQ ID NO: 39)
5'-AGACCCAGACCCAGACCCACAANNANNANNCATANNANNANNANNA
NNANNANNCATANNANNCATGGATATATCTCCTACTTAAA-3'

VB1-7:
(SEQ ID NO: 40)
5'-AGACCCAGACCCAGACCCACAANNANNANNCATANNANNANNANNA
NNCATANNANNANNCATGGATATATCTCCTACTTAAAG-3'

VB1-8:
(SEQ ID NO: 41)
5'-AGACCCAGACCCAGACCCACAANNANNANNCATANNANNANNANNA
NNANNCATANNANNANNCATGGATATATCTCCTACTTAAAG-3'

VB1-9:
(SEQ ID NO: 42)
5'-AGACCCAGACCCAGACCCACAANNANNANNCATANNANNANNANNA
NNANNANNCATANNANNANNCATGGATATATCTCCTACTTAAG-3'

VB2-1:
(SEQ ID NO: 43)
5'-AGACCCAGACCCAGACCCACACATANNANNANNANNCATANNA
NNCATGGATATATCTCCTACTTAAAG-3'

VB2-2:
(SEQ ID NO: 44)
5'-AGACCCAGACCCAGACCCACACATANNANNANNANNANNANNCATA
NNANNCATGGATATATCTCCTACTTAAAG-3'

VB2-3:
(SEQ ID NO: 45)
5'-AGACCCAGACCCAGACCCACACATANNANNANNANNANNANNANNN
CATANNANNCATGGATATATCTCCTACTTAAAG-3'

VB-4:
(SEQ ID NO: 46)
5'-AGACCCAGACCCAGACCCACACATANNANNANNANNANNCATANNA
NNANNCATGGATATATCTCCTACTTAAAG-3'

VB2-5:
(SEQ ID NO: 47)
5'-AGACCCAGACCCAGACCCACACATANNANNANNANNANNANNCATA
NNANNANNCATGGATATATCTCCTACTTAAAG-3'

VB2-6:
(SEQ ID NO: 48)
5'-AGACCCAGACCCAGACCCACACATANNANNANNANNANNANNANNC
ATANNANNANNCATGGATATATCTCCTACTTAAAG-3'

VB2-7:
(SEQ ID NO: 49)
5'-AGACCCAGACCCAGACCCACACATANNANNANNANNANNCATANNA
NNANNANNCATGGATATATCTCCTACTTAAAG-3'

VB2-8:
(SEQ ID NO: 50)
5'-AGACCCAGACCCAGACCCACACATANNANNANNANNANNANNCATA
NNANNANNANNCATGGATATATCTCCTACTTAAAG-3'

VB2-9:
(SEQ ID NO: 51)
5'-AGACCCAGACCCAGACCCACACATANNANNANNANNANNANNANNC
ATANNANNANNANNCATGGATATATCTCCTACTTAAAG-3'

VBP.F49:
(SEQ ID NO: 52)
5'-TAATACGACTCACTATAGGGTTGAACTTTAAGTAGGAGATATATCC
ATG-3'

VBP.R39:
(SEQ ID NO: 53)
5'-TTTCCGCCCCCCGTCCTAAGACCCAGACCCAGACCCACA-3'

1-3. FIT System

A FIT system was prepared as a mixture containing all the ingredients necessary for translation except methionine and RF1. The FIT system has the following composition: 50 mM HEPES-KOH (pH 7.6); 12 mM magnesium acetate; 100 mM potassium acetate; 2 mM spermidine; 20 mM creatinine phosphate; 2 mM DTT; 2 mM ATP; 2 mM GTP; 1 mM CTP; 1 mM UTP; 0.1 mM 10-formyl-5,6,7,8-tetrahydrofolic acid; 0.5 mM proteinogenic amino acids other than 15 Met, Lys, Gln, Trp, and Glu; 1.5 mg/ml E. coli total tRNA; 0.73 µM AlaRS; 0.03 µM ArgRS; 0.38 µM AsnRS; 0.13 µM AspRS; 0.02 µM CysRS; 0.06 µM GlnRS; 0.23 µM GluRS; 0.02 µM GlyRS; 0.02 µM HisRS; 0.4 µM IleRS; 0.04 LeuRS; 0.11 µM LysRS; 0.03 µM MetRS; 0.68 µM PheRS; 0.16 µM ProRS; 0.04 µM SerRS; 0.09 µM ThrRS; 0.03 µM TrpRS; 0.02 µM TyrRS; 0.02 µM ValRS; 0.6 µM MTF; 2.7 µM IF1; 0.4 µM IF2; 1.5 µM IF3; 0.26 µM EF-G; 10 µM EF-Tu; 10 µM EF-Ts; 0.25 µM RF2; 0.17 µM RF3; 0.5 µM RRF; 0.1 µM T7 RNA polymerase; 4 µg/ml creatine kinase; 3 µg/ml myokinase; 0.1 µM pyrophosphatase; 0.1 µM nucleotide-diphosphatase kinase; and 1.2 µM ribosome.

1-4. Preparation of tRNAf$^{Met}_{CAU}$, tRNa$^{Asn-E2}_{CCA}$, and Flexyzyme tRNAf$^{Met}_{CAU}$: P1 and P2 were annealed, and then extended using Taq DNA polymerase. The resulting product was diluted to 20 times with a PCR reaction liquid and amplified using P3 and P4 as 5'- and 3'-primers, respectively. The amplified product was diluted to 200 times with a PCR reaction liquid and was amplified using P3 and P5 as 5'- and 3'-primers, respectively. The DNA product thus obtained was transcribed using T7 RNA polymerase and purified with 10% denatured PAGE. The tRNAf$^{Met}_{CAU}$ thus purified was dissolved in water.

tRNa$^{Asn-E2}_{CAU}$: P6 and P7 were annealed, and then extended using Taq DNA polymerase. The double stranded DNA (dsDNA) thus obtained was diluted to 20 times with a PCR reaction liquid and amplified with P3 and P8 as 5'- and 3'-primers, respectively. Further, the amplified product was diluted to 200 times with a PCR reaction liquid and amplified with P3 and P9 as 5'- and 3'-primers, respectively. The DNA product was transcribed using T7 RNA polymerase and purified by a denatured PAGE. The tRNa$^{Asn-E2}_{CAU}$ thus purified was dissolved in water.

Flexizyme (eFx): P10 and P11 were annealed and then extended using Taq DNA polymerase. The double stranded DNA (dsDNA) thus obtained was diluted to 20 times with a PCR reaction liquid and was amplified with P3 and P12 as 5'- and 3'-primers, respectively. The amplified product was diluted to 200 times with a PCR reaction liquid and was amplified with P3 and P9 as 5'- and 3'-primers, respectively. The DNA product was transcribed using T7 RNA polymerase and purified with denatured PAGE. The eFX thus purified was dissolved in water.

tRNa$^{Asn-E2}_{CCA}$: P6 and P13 were annealed and then extended using Taq DNA polymerase. The double stranded DNA (dsDNA) thus obtained was diluted to 20 times with a PCR reaction liquid and was amplified with P3 and P8 as 5'- and 3'-primers, respectively. Further, the amplified product was diluted to 200 times with a PCR reaction liquid and was amplified with P3 and P9 as 5'- and 3'-primers, respectively. The DNA product was transcribed using T7 RNA polymerase and purified with denatured PAGE. The $^{Asn-E2}_{CCA}$ thus purified was dissolved in water.

1-5. Chloroacetyl-D-Phenylalanine-CME 0.3 mL of a 50% 1,4-dioxane aqueous solution containing phenylalanine (33 mg, 0.20 mmol), acetic acid N-hydroxysuccinimide (38 mg, 0.24 mmol), and NaHCO$_3$ (50 mg, 0.60 mmol) was stirred at room temperature for one hour. After the reaction, 1,4-dioxane was evaporated and the solution was washed with AcOEt (3 mL×2). The aqueous layer was acidified with 1 M HCl and extracted with ethyl acetate (3 mL×2), while the organic layer was dried over MgSO$_4$ and concentrated under reduced pressure. The residue (Nα-Ac-Phe-OH) was mixed with Et3N (24 mg, 0.24 mmol) in 0.2 mL of DMF and chloroacetonitrile (0.1 mL) and the reaction mixture was stirred at room temperature for 12 hours. After the reaction, Et20 (9 mL) was added. The resulting mixture was washed with 1 M HCl (3 mL×3), saturated NaHCO3 (3 mL×3), and brine (5 mL×1). The organic layer was dried over MgSO$_4$ and concentrated under reduced pressure. The residue was purified by silica gel column chromatography to obtain Nα-ClAc-Phe-CME (28 mg, over all yield 55%).

$^1$H NMR (CDCl3, 500 MHz) δ 7.35 (m, 3H), 7.16 (d, J=7.0 Hz, 2H), 5.9 (br, 1H), 4.95 (m, 1H) 4.81 (d, J=15.6 Hz, 1H), 4.71 (d, J=15.6 Hz, 1H), 3.17 (m, 2H), 2.02 (s, 3H).

1-6. Chemical Synthesis of Nle-CME

To an N-butoxycarbonyl-L-norleucine solution in N,N'-dimethylformamide (0.2 ml) was added a solution of Et3N (56 mg, 0.55 mmol) and chloroacetonitrile (0.1 mL). The mixture was stirred at room temperature for 14 hours. After the reaction, the precipitate was filtered and the resulting solution was washed with saturated NaHCO$_3$ (3 mL×3) and brine (5 mL×1). The organic layer was dried over MgSO$_4$ and concentrated under reduced pressure. The residue was purified by silica gel column chromatography to obtain N-butoxycarbonyl-L-norleucine cyanomethylmethyl ester.

The purified product was dissolved in 2 mL of 4N HCl/ethyl acetate and the resulting solution was incubated at room temperature for 15 minutes. After the solution was concentrated under reduced pressure, addition of diethyl ether (3 mL) and concentration under reduced pressure were repeated three times and the remaining HCl was removed. Diethyl ether (3 mL) was added to the product thus obtained to cause precipitation. The precipitate was filtered to obtain Nle-CME (59.0 mg, 0.285 mmol, overall quantitative yield).

$^1$H NMR (CDCl3, 500 MHz) δ 8.03 (m, 3H), 5.19 (s, 1H), 4.59 (s, 1H), 4.17 (m, 1H) 1.81 (s, 2H), 1.31 (m, 2H), 1.11 (m, 2H), 0.88 (m, 3H).

1-7. Chemical Synthesis of Ahep-CME

To a solution of (S)-2-[(t-butoxycarbonyl)amino]heptanoic acid (68 mg, 0.26 mmol) in N,N'-dimethylformamide (0.2 ml) was added a solution of Et3N (56 mg, 0.55 mmol) and chloroacetonitrile (0.1 mL). The resulting mixture was stirred at room temperature for 14 hours and the precipitate was filtered. The filtrate was washed with saturated NaHCO$_3$ (3 mL×3) and brine (5 mL×1). The organic layer was dried over MgSO$_4$ and reduced under reduced pressure. The residue was purified by silica gel column chromatography to obtain (S)-2-[(t-butoxycarbonyl)amino]heptanoic acid-CME. The purified product was dissolved in 2 mL of 4N HCl/ethyl acetate, followed by incubation at room temperature for 15 minutes. After concentration under reduced pressure, addition of diethyl ether (3 mL) and concentration under reduced pressure were performed three times to remove the remaining HCl. Diethyl ether was added to the product thus obtained to cause precipitation. The precipitate was filtered to obtain Ahep-CME (23.1 mg, 0.103 mmol, overall 57% yield).

$^1$H NMR (CDCl3, 500 MHz) δ 8.33 (s, 3H), 4.58 (s, 2H), 4.10 (s, 1H), 1.82 (s, 2H), 1.40 (m, 2H), 1.28 (m, 4H), 0.88 (m, 3H).

1-8. Preparation of $^{ClAc-D}$-F-tRNAf$^{Met}_{CAU}$

3 μL of 41.7 μM tRNA$^{fMet}_{CAU}$ and 3 μL of 41.7 μM eFx were heated at 95° C. for 2 minutes in 167 mM HEPES-KOH (pH 8.0). The reaction mixture was then cooled to room temperature for 5 minutes. To the resulting RNA solution was added 2 μL of 3M MgCl$_2$. The resulting mixture was incubated on ice for 5 minutes. Then, 2 μL of 25 mM $^{ClAc-D}$-F-CME (in DMSO) was added and the resulting mixture was incubated over ice for one hour. The reaction was then terminated with 40 μL of 0.3M sodium acetate (pH 5.2) and tRNA was recovered by ethanol precipitation. The precipitate was washed twice with 70% ethanol and 0.1M sodium acetate (pH 5.2) and once with 70% ethanol. After air drying for 10 minutes, the precipitate was dissolved in 1.0 μL of 0.1 mM sodium acetate. The resulting solution was used for a 5.0 μL-scale translation reaction.

1-9. Preparation of Ahep-tRNA$^{Asn-E2}_{CCA}$ and Ahep-tRNA$^{Asn-E2}_{CAU}$

In 167 mM HEPES-KOH (pH 8.0), 3 μL of 41.7 μM tRNA$^{Asn-E2}_{CCA}$ and 3 μL of 41.7 μM eFx were heated at 95° C. for 2 minutes and then, cooled to room temperature for 5 minutes. To the resulting RNA solution was added 2 μL of 3 M MgCl$_2$, followed by incubation on ice for 5 minutes. Then, 2 μL of 25 mM Ahep-CME (in DMSO) was added to the reaction mixture, followed by incubation on ice for 3 hours. The reaction was terminated with 40 μL of 0.3 M sodium acetate (pH5.2) and the tRNA was recovered by ethanol precipitation. The precipitate was washed twice with 70% ethanol and 0.1 M sodium acetate (pH 5.2) and then once with 70% ethanol. After air drying for 10 minutes, the precipitate was dissolved in 1.0 μL of 0.1 mM sodium acetate and the resulting solution was used for a 5.0 μL-scale translation reaction.

Ahep-tRNA$^{Asn-E2}_{CAU}$ was prepared similarly except for the use of tRNA$^{Asn-E2}_{CAU}$ instead of tRNA$^{Asn-E2}_{CCA}$.

1-10. Analysis of Aminoacylation

Aminoacylation of tRNA by $^{ClAc-D}$-F-CME and Ahep-CME was analyzed in accordance with the conventional method (H. Murakami, A. Ohta, H. Ashigai, H. Suga (2006) Nature Methods 3, 357-359.). Pellets containing 10 μmol tRNA after aminoacylation were dissolved in 3.5 μL of a 0.4 M Hepes-K (pH 8.0) solution of 7.5 mg/mL of sulfosuccinimidyl-D-biotin (Dojin, Japan). Biotinylation reaction was performed for one hour on ice. The reaction was terminated with 8.0 μL of 0.6 M sodium acetate (pH 5.0), followed by precipitation with ethanol. The pellets were washed twice with 70% ethanol (pH 5.0) containing 0.1 M sodium acetate and dissolved in 10.0 μL of H$_2$O. The resulting solution (0.5 μL) was mixed with 1.5 μL of a loading buffer (0.2 mg/mL of streptavidin (in 37 mM piperazine (pH 6.1)), 37 mM EDTA, and 6 M urea) and the resulting mixture was analyzed with 12% denatured PAGE containing 6 M urea. The RNA was stained with Syber Green II (Molecular Probe) and observed using FLA-5100 (Fuji, Japan).

1-11. Preparation of a Template DNA Model Encoding the Macrocyclic Peptide (which Will Hereinafter be Called "VB Peptide") of the Present Invention M1 and M2 were annealed and then extended using Taq DNA polymerase. The product thus obtained was diluted to 100 times with a PCR reaction liquid and was amplified with M3 and M4 as 5'- and 3'-primers, respectively. Further, the amplified product was diluted to 100 times with a PCR reaction liquid and was amplified with M3 and M5 as 5'- and 3'-primers, respectively. The PCR product was purified by extraction with phenol/chloroform and precipitated with ethanol. The purified DNA was dissolved in water.

1-12. Translational Synthesis of Model VP Peptide

A FIT system to which the template DNA, 100 μM $^{ClAcD}$F-tRNA$^{fMet}_{CAU}$ and 200 μM Ahep-tRNA$^{Asn-E2}_{CAU}$ had been added was incubated at 37° C. for 30 minutes. The translation product was poured in SPE C-TIP (Nikkyo technos Co., Tokyo, Japan) filled with C18 silica, washed twice with 4% acetonitrile and 0.5% acetic acid, eluted with 80% acetonitrile and 0.5% acetic acid, and then analyzed using MALDI-TOF mass.

1-13. MADLI-TOF Analysis of Translated Peptide

MALDI-TOF analysis was performed using Autoflex II (Bruker Daltonics) and peptide calibration standard II (Bruker Daltonics).

1-14. Preparation of VB mRNA Library VB1 mRNA library

A VB1 DNA library was prepared by a 2-step reaction. First, a forward primer VF and each of reverse primers VB1-1, VB1-2, VB1-3, VB1-4, VB1-5, VB1-6, VB1-7, VB1-8 and VB1-9 were annealed and then extended using Taq DNA polymerase. The template DNAs thus obtained were amplified by a 5-cycle PCR using VF and a reverse primer VR. The resulting template DNAs were provided for in vitro transcription using T7 RNA polymerase. The respective mRNAs (VB1-1: VB1-2: VB1-3: VB1-4: VB1-5: VB1-6: VB1-7: VB1-8: VB1-9) were mixed at a molar ratio of 1/16$^2$: 1/16: 1: 1/16: 1: 1: 1: 1: 1 and the concentration was adjusted to 10 mM.

VB2 mRNA Library

A VB2 DNA library was prepared similarly to the VB1 DNA library. A forward primer VF and each of reverse primers VB2-1, VB2-2, VB2-3, VB2-4, VB2-5, VB2-6, VB2-7, VB2-8 and VB2-9 were annealed and then extended using Taq DNA polymerase. The template DNAs thus obtained were amplified by a 5-cycle PCR using VF and a reverse primer VR. The template DNAs were provided for in vitro transcription using T7 RNA polymerase. The respective mRNAs (VB2-1: VB2-2: VB2-3: VB2-4: VB2-5: VB2-6: VB2-7: VB2-8: VB2-9) were mixed at a molar ratio of 1/16$^2$: 1/16$^2$: 1/16$^2$: 1/16$^2$: 1/16$^2$: 1/16: 1/16$^2$:1/16:1 and the concentration was adjusted to 10 mM.

2. Results 2-1. Aminoacylation with $^{ClAc-D}$-F-CME, Nle-CME, and Ahep-CME using Flexizyme System An aminoacylation efficiency of $^{ClAc-D}$-F-CME, Nle-CME, and Ahep-CME by using Flexyzyme was verified in accordance with a standard protocol of the present inventors. As a result, tRNA analogs were charged with these CMEs, respectively. An initiator tRNA$^{fMet}_{CAU}$ was charged with $^{ClAc-D}$-F-CME and elongator tRNA$^{Asn-E2}_{CCA}$ was charged with each of Nle-CME and Ahep-CME. As Flexizyme, eFx was used.

Three amino acid analogs were each sufficiently and efficiently incorporated in a polypeptide to be elongated. The aminoacylation efficiency of Ahep-CME was 1.2 times higher than that of Nle-CME. Next, Nle and Ahep were incorporated in a specific site of the model peptide and the respective peptides containing Nle and Ahep were measured by a peptide determination method using radioisotope. The peptide concentration was determined by comparing a count of [14C]-Asp radioisotope (RI) with a count of a known concentration. The concentration of each peptide was determined by applying an RI count of each of an expressed wild type peptide and macrocyclic peptide to a calibration line. The model peptides containing Nle and Ahep, respectively, showed an equivalent level of expression, but Ahep was used for subsequent experiments because it had a longer fatty acid chain than Nle.

2-2. Comparison Between VB Peptide Model and Control

To indicate effectiveness of the FIT system for the preparation of a VB peptide, a model sequence to be expressed using the FIT system was designed. First, with $^{ClAc-D}$-F-CME and Ahep-CME as a material, tRNA$^{fMet}_{CAU}$ and tRNA$^{Asn-E2}_{CCA}$ were charged with $^{ClAc-D}$-F and Ahep, respectively.

Those aminoacyl tRNAs were added to the Met-free FIT system. A template DNA including a code sequence AUG-UGG-ACC-AAG-UCU-AUU-CCG-CCG-AUU-UGG-UUU-CCG-GAC-UGU-GAC-UAC-AAG-GAC-GAC-GAC-GAC-AAG-UAA (SEQ ID NO: 54) was transcribed and translated in the FIT system.

An initiator AUG codon and an elongator UGG codon were decoded as $^{ClAc-D}$-F-tRNA$^{fMet}_{CAU}$ and Ahe-tRNA$^{Asn-E2}_{CCA}$, respectively, so that a VB peptide $^{ClAc-D}$FAhepTKSIPPIAhepFPDCDYKDDDDK (SQ ID NO: 55) was produced.

As has previously been reported, when $^{ClAc-D}$F is expressed at the initiator AUG, a macrocyclic peptide is formed easily by a spontaneous reaction between an N-terminal chloroacetyl group and a sulfhydryl group of C-terminal cysteine. Two Ahep residues expressed at the UGG codon form a pseudo bicyclic like structure in an expressed peptide. Expression of a VB peptide containing two Ahep residues has been confirmed by MALDI-TOF mass analysis.

The following macrocyclic model peptide sequence similar to the VB peptide except for the use of a Ser residue instead of the Ahep amino acid residue was designed as a negative control for VB synthesis experiment and translation was performed in the Met-free FIT system while assigning the AUG codon to $^{ClAc-D}$F-tRNA$^{fMet}_{CAU}$. As a result, a linear peptide having the following sequence was expressed and spontaneously cyclized into a macrocyclic peptide.

(SEQ ID NO::56)
$^{ClAc-D}$-F<u>S</u>TKSIPPI<u>S</u>FPDCDYKDDDDK

MALDI-TOF mass analysis of the resulting peptide revealed that it required longer time for cyclization than the VB peptide. This suggests that hydrophobic interaction of the non-proteinogenic alkyl chain in the VB peptide, spontaneous cyclization occurred more rapidly in this peptide than in the non-VB peptide.

2-3. Construction of VB mRNA Library

Based on success in translational incorporation of $^{ClAc-D}$F and Ahep by using flexizyme, two respectively different mRNA libraries (which will hereinafter be called "VB-1 mRNA library" and "VB-2 mRNA library", respectively) were constructed. First, a double-stranded DNA pool was constructed from a synthetic template DNA having random nucleotide sequences introduced by a (NTT)x codon (in which N represents A, T, G, or C and X stands for an integer of any of from 7 to 14). These random sequences were placed between an initiator ATG codon for $^{ClAc-D}$F, two elongator ATG codons for Ahep, and a TGT codon for C-terminal cysteine.

An ATG codon was assigned to each of codons encoding a non-proteinogenic amino acid. Only one difference between the VB-1 mRNA library and the VB-2 mRNA library was a position of the elongator ATG codon that expresses an Ahep amino acid (FIG. 2). A VB skeleton more suited for screening of a peptide inhibitor against a target protein was studied by constructing two libraries.

From these DNA libraries, an mRNA pool was prepared by in vitro transcription. In these NNU mRNA libraries, 15 proteinogenic amino acids were assigned to 16 active codons and as an initiator amino acid, a D-form amino acid was selected in order to enhance the protease resistance of the VB peptide. In addition, by omitting a stop codon from a random region in both the libraries, reliability of VB peptide library production was enhanced. Both the mRNA libraries included a T7 promoter (5'-UAAUACGACUCA-CUAUAG-3'; SEQ ID NO: 57), an epsilon sequence (5'-UUAACUUUAA-3'; SEQ ID NO: 58), a Shine-Dalgarno sequence (5'-AAGGAGA-3'; SEQ ID NO: 59), a random NNU region (FIG. 2), a linker sequence (5'-GGCAGCG-GCAGCGGCAGC-3'; SEQ ID NO: 60), and a sequence complementary to puromycin linker (5'-UAG-GACGGGGGCGGAAA-3'; SEQ ID NO: 61).

2-4. Conclusion

The present inventors succeeded in ribosome synthesis of the VB peptide and development of an mRNA library for expression of a peptide having a VB skeleton. In designing a VB mRNA library, two respectively different VB skeletons were prepared by assigning Ahep to places different in mRNA sequence. Using an mRNA library that expresses two respectively different VB peptides is presumed to increase the possibility of success in screening of a peptide inhibitor against a therapeutic target.

B. In Vitro Screening of a PAD4 Inhibitor Using the Macrocyclic Peptide Library of the Present Invention 1. Material and Method 1-1. Oligonucleotide Primer The following oligonucleotide primers were used. They were all purchased from Operon Biotechnologies (Japan).

VF:
(SEQ ID NO: 62)
5'-TAATACGACTCACTATAGGGTTGAACTTTAAGTAGGAGATATATCCATG-3'

VR:
(SEQ ID NO: 63)
5'-TTTCCGCCCCCGTCCTAAGACCCAGACCCAGACCCACA-3'

1-2. Selection by RaPID Display Method

Oligo DNA (5'-pCTCCCGCCCCCCGTCC-3'; SEQ ID NO: 64) was bound to 200 pm of each mRNA of the mRNA library. The oligo DNA has, at the 3' end thereof, puromycin-CC-PEG. The mRNA-puromycin thus obtained was incubated at 37° C. for 60 minutes in 150 μL of a FIT system not containing RF1 and Met but containing 50 μM $^{ClAc-D}$F-tRNA$^{fMet}_{CAU}$ and 100 μM Ahep-tRNA$^{Asn-E2}_{CAU}$. The reaction mixture was incubated further at room temperature for 12 minutes to reinforce a peptide-mRNA bond via puromycin.

Then, 15 μL of 100 mM EDTA [pH 7.5] was added to the resulting solution to dissociate the ribosome from the peptide-mRNA bond. The macrocyclization of the peptide was promoted by further incubation at 37° C. for 30 minutes. After removal of EDTA by gel permeation chromatography (GPC), 165 μL of a blocking solution (100 mM Tris-HCl [pH 7.6], 1.3 M NaCl, 0.1% tween, 0.2% acetyl BSA, and 5 μM tRNA) was added to the reaction mixture.

The reaction mixture was mixed with 6 mg of Dynabeads magnetic beads (Invitrogen) and the resulting mixture was incubated at 4° C. for 30 minutes in order to remove a His-tag-containing protein in the FIT system and a peptide that binds to beads in the peptide library. After incubation, the resulting beads were washed. They were incubated again at 4° C. for 30 minutes with 1.2 mg of Dynabeads (this repeated process will hereinafter be called "pre-clear")". Then, the library and His-PAD4 immobilized to the Dinabeads were mixed. After the resulting mixture was incubated at 4° C. for 1 hour, a PAD4-bound peptide was selected.

The concentration of the His-PAD4 in the above incubation was set at 400 nM. The supernatant was removed and the beads were washed twice with 800 μL of TBS-T (50 mM Tris-HCl [pH 8.0], 150 mM NaCl, 0.05% tween 20). The beads were mixed with 40 μL of a reverse-transcription mix (0.6 mM dNTP, 2.5 μM oligo DNA 012, and M-MLV Reverse Transcriptase (Promega) (in a reaction buffer sold as a set with a reverse transcriptase)) and the resulting mixture was incubated at 42° C. for 1 hour. To a suspension of the beads was added 200 μL of a PCR reaction liquid (10 mM Tris-HCl [pH 9.0], 50 mM KCl, 0.1% Triton X-100, 2.5 mM MgCl$_2$, 0.25 mM dATP, 0.25 mM dTTP, 0.25 mM dGTP, 0.25 mM dCTP, 0.25 μM oligo DNA VF, and 0.25 μM oligo DNA VR) and the reaction mixture was heated at 95° C. for 5 minutes.

The supernatant was transferred to a new tube and mixed with 600 μL of a PCR reaction liquid.

The reaction mixture (20 μL) was provided for real time PCR for determining the amount of DNA recovered after binding selection. The remaining DNA was amplified by PCR with oligo DNA VF and VR as 5'- and 3'-primers, respectively. The DNA thus amplified was transcribed to build an mRNA library in which a sequence to be bound to PAD4 had been enriched and the library was used for the selection of a subsequent round.

The second round and rounds thereafter were performed essentially in a procedure similar to that of the first round except for the following points.

(1) A translation amount was reduced to 5 μL.

(2) In order to efficiently remove the peptide bound to the beads, pre-clear time was increased. First, a translation product was incubated with 0.3 mg of Dynabeads at 4° C. for 30 minutes and the supernatant was incubated with 0.1 mg of dynabeads TALON twice at 4° C. for 30 minutes (pre-clear was performed three times in total).

(3) Reverse transcription was performed before binding selection using M-MLV Reverse Transcriptase, RNase H Minus [Point Mutant] (Promega) to prevent an RNA-aptamer from being selected.

(4) After the selection, cDNA of the PAD4-bound peptide was recovered using 100 μL of a PCR reaction liquid. A 1⁄4 portion of 100 μL of the recovered cDNA was used for real time PCR for determining the amount of the selected sequence and the remaining 99 μL was amplified by PCR. After enrichment of the PAD4-bound sequence, the dsDNA sequence was cloned by standard TA cloning method while using a pGEM-T easy vector (Promega) and the sequence was determined using BigDye Terminator v3.1 (Life Technologies).

1-3. MALDI-TOF Analysis

For any of MALDI-TOF analyses, Autoflex II (Bruker Daltonics) and peptide calibration standard II (Bruker Daltonics) were used.

1-4. Peptide Synthesis of VB Peptide by Fmoc Solid-Phase Synthesis

Peptides were synthesized from the C terminal by a standard Fmoc solid-phase synthesis process. Described specifically, first, Rink amide AM resin (25 μmol scale) (Merck) was incubated at room temperature while rotating it with 40% piperidine in N,N-dimethylformamide (DMF) for 3 minutes. Then, the Fmoc group was removed by incubating while rotating the resin with 20% piperidine in DMF at room temperature for 12 minutes. After washing with DMF (2 mL, five times), the resin was incubated by rotating it at room temperature for 40 minutes in a solution containing 0.19 M Fmoc-Cys, 0.19 M 2-(1H-benzotriazol-1-yl)-1,1,3,3-tetramethyluronium hexafluorophosphate (HBTU) and 1-hydroxybenzotriazole (HOBt), and 0.38 M N,N-diisopropylethylamine (DIEA). After the resin was washed with DMF (2 mL, three times), Fmoc removal and binding of amino acids were repeated until binding of the N-terminal amino acid or D-Phe. Their Fmoc was also removed.

In synthesis of VB1C12 peptide and VB1C20 peptide selected, the N-terminal α-amino group of the peptide synthesized on the resin was chloroacetylated by incubating it with a solution containing 0.5 M chloroacetyl N-hydroxysuccinimide (NHS) ester in N-methylpyrrolidone (NMP), while rotating them at room temperature for 40 minutes.

After washing with DMF (2 mL, three times), the resin was incubated with trifluoroacetic acid solution (TFA)/1,2-ethanedithiol/triisopropylsilane/water (92.5:2.5:2.5:2.5) at room temperature for 3 hours to cleave the peptide from the resin and deprotect it.

The peptide thus cleaved was precipitated with diethyl ether, pelletized by centrifugal treatment, and washed with diethyl ether (3 mL, five times).

The crudely purified peptide was dissolved in a water/acetonitrile (1:1) solution containing 0.1% TFA. The pH of the solution was adjusted to about pH 10 with triethylamine. The resulting mixture was incubated while rotating it at 42° C. for 2 hours to promote thioether bonding between the N-terminal chloroacetamide group and the sulfonyl group of cysteine.

The peptide solution was then acidified with TFA and purified to a purity exceeding 95% by reverse phase HPLC (Cosmosil, 5C18-AR-300, 10×250 mm, Nacalai tesque) using a water-acetonitrile gradient. After removal of acetonitrile from the peptide by using a rotary evaporator, the residue was lyophilized. The selected peptide was dissolved in DMSO and provided as a stock solution. The peptide for stock was diluted with water containing 50% (v/v) acetonitrile and the concentration was determined by a spectrophotometer. The purified peptide was lyophilized and dissolved in DMSO. All the peptides thus synthesized were analyzed using MALDI-TOF mass to confirm their molecular weight.

1-5. Analysis of Binding Reaction Rate (Binding Kinetics) Analysis by Surface Plasmon Resonance (SPR)

Analysis of a reaction rate was performed at 25° C. using Biacore T100 instrument (GE healthcare) and a Ni-NTA sensor chip. His-PAD4 was immobilized on a chip surface. In any experiment, modified HBS-EP+(10 mM HEPES-KOH [pH 7.4], 150 mM NaCl, 50 μM EDTA, 0.05% Tween 20, 0.1% DMSO) was used as a running buffer. The reaction rate data were corrected by injecting five peptides having respectively different concentrations for one minute at a flow rate (10 mM HEPES-KOH [pH 7.4], 150 mM NaCl, 50 μM EDTA, 0.05% Tween 20, 0.1% DMSO). Peptide dissociation was performed for one minute during injection and for 3 minutes after the last injection.

Background binding was monitored by performing blank buffer injection twice before sample injection and once after sample injection in order to double reference with the surface of a negative control having no His-PAD4 bound thereto but having nickel. The binding sensorgram, the binding sensorgram was analyzed using the Biacore software.

1-6. Cl-Amidine

Commercially available Cl-amidine (CAS 913723-61-2) was purchased from Cayman Chemical Company, USA.

1-7. Human PAD4 Enzyme

Human PAD4 was purchased from Modiquest Research (catalog no. MQ 16.206-10). Human PAD4 is a protein having NCBI accession no. CCDS180.1, a molecular weight of 74.08 kDa, and 663 amino acids.

1-8. In Vitro PAD4 Inhibition Assay

PAD4 inhibition assay was performed using various concentrations of VB peptides in a reaction buffer containing 100 mM HEPES (pH 7.6) and 50 mM NaCl.

Before reaction was initiated by adding BAEE (final concentration: 10 mM), the above reaction mixture was incubated with PAD4 (0.2 μM) (in the presence of 5 mM $CaCl_2$) at 37° C. for 15 minutes. After reaction for 30 minutes, the reaction was terminated by flash freezing in liquid nitrogen. For color development, 200 μL of a freshly prepared COLDER solution (2.25 M $H_3PO_4$, 4.5 M $H_2SO_4$, 1.5 mM $NH_4Fe(SO_4)$, 20 mM diacetyl monoxime, and 1.5 mM thiosemicarbazide) was added to each of the reaction terminated solutions. The resulting mixture was vortexed to ensure complete mixing and then, incubated at 95° C. for 30 minutes (Firestein, G. S., 2003, Nature, 423(6937), 356-61; Jones, J. E., et al., ACS chemical biology, 7(1), 160-5). The absorbance at 540 nm was measured. Compared with a standard curve of Cit, the concentration of Cit produced during the reaction was determined.

1-9. Chemical Modification of VB1C 12 Peptide for Cl-Amidine Warhead Introduction (1) Fmoc Solid-Phase Synthesis Peptide Synthesis A VB1C12 peptide was synthesized from the C terminal by a standard Fmoc solid-phase synthesis process. Described specifically, first, Rink amide AM resin (25 μmol scale) (Merck) was incubated at room temperature while rotating it with 40% piperidine in N,N-dimethylformamide (DMF) for 3 minutes. Then, the Fmoc group was removed by rotating the resin with 20% piperidine in DMF at room temperature for 12 minutes. After washing with DMF (2 mL, five times), the resin was incubated by rotating it at room temperature for 40 minutes in a solution containing, in DMF, 0.19 M Fmoc-cysteine, 0.19 M 2-(1H-benzotriazol-1-yl)-1,1,3,3-tetramethyluronium hexafluorophosphate (HBTU) and 1-hydroxybenzotriazole (HOBt), and 0.38 M N,N-diisopropylethylamine (DIEA). After the resin was washed with DMF (2 mL, three times), Fmoc removal and binding of amino acids were repeated until binding of the N-terminal amino acid or D-Phe. Their Fmoc was also removed.

(2) Binding of Chloroacetyl N-Hydroxysuccinimide (NHS)

The N-terminal α-amino group of the peptide synthesized on the resin was chloroacetylated by incubating while rotating it with a solution containing 0.5M chloroacetyl n-hydroxysuccinimide (NHS) ester in N-methylpyrrolidone (NMP) at room temperature for 40 minutes.

The resin was washed with DMF (2 mL, three times) and similarly washed with DCM.

(3) Removal of Mmt Group from Cys Residue and Macrocyclization

Incubation of the resin in a 1% TFA dichloromethane solution for 15 minutes was performed six times to remove the Mmt group from the C-terminal Cys residue. For macrocyclization of the peptide on the resin, the resin was incubated with 20% DIPEA/DMF at room temperature for 2 hours. After completion of macrocyclization, the resin was washed with DCM (2 ml, three times).

(4) Removal of Alloc Group from Ornithine Bound to Resin

Tetrakis(triphenylphosphine)palladium (0.1 equiv per Alloc moiety) and N,N-dimethylbarbituric acid (5 equiv per Alloc moiety) were put in an amino acid vial washed with argon. Next, 4.5 mL of DCM was added to the amino acid vial to dissolve the solid. The resulting solution was transferred to a reaction vessel and the vessel was agitated for 2 hours. The whole procedure was performed again and then the resin was washed three times with DCM, three times with 0.2M DIEA (in DMF), and six times with DMF.

(5) Functionalization of $\delta NH_2$ of Ornithine Bound to the Resin

Methyl 2-chloroacetoimidate hydrochloride (5.5 mmol), dry triethylamine (5.5 mmol), and resin-bound ornithine (1.23 mmol) were mixed with 1 ml of dry DMF. The reaction mixture was stirred overnight (16 hours) at room temperature under argon. Next, the resin was filtered and successively washed with DMF and DCM.

(6) Cleavage of Final Product from Resin

By incubating with a mixture for cleavage (containing TFA: 1,2-ethanedithiol: triisopropyl silane: water at 92.5:2.5:2.5:2.5) at room temperature for 3 hours, the final product was deprotected and cleaved from the resin.

Next, the peptide was precipitated in diethyl ether and pelletized by manual centrifugation treatment. The crudely purified peptide was dissolved in a water:acetonitrile (4:1) solution containing 0.1% TFA.

The peptide was then purified to a purity exceeding 95% by reverse phase HPLC (Cosmosil, 5C18-AR-300, 10×250 mm, Nacalai tesque) using a water-acetonitrile gradient. After removal of acetonitrile from the peptide by a rotary evaporator, the residue was lyophilized. The selected peptide was dissolved in DMSO and the resulting solution was used as a stock solution. The stock peptide was diluted with water containing 50% (v/v) acetonitrile and its concentration was determined using a spectrophotometer. The peptide thus purified was lyophilized and dissolved in DMSO. All the peptides thus synthesized were analyzed using MALDI-TOF mass to confirm their molecular weight (cal. mass=1801.48, obs. mass=1800.17).

1-10. Chemical Synthesis of Fluorescently-Labeled Peptide

Fluorescently-labeled peptides were all chemically synthesized by the above-mentioned Fmoc solid-phase peptide synthesis. In all the peptides, an additional Lys residue was introduced into the C-terminal by a B-alanine linker. After Fmoc removal of the N-terminal amino acid, the resin was incubated with 0.5M chloroacetyl-NHs/NMP at room temperature for 40 minutes.

The resin was washed with dichloromethane. The resin was then incubated with a 1% TFA dichloromethane solution six times in 15 minutes to remove the Mmt group from the C-terminal Lys residue. The residue was incubated with 50 mM fluorescence-NHS in NMP/DIPEA in a dark place. The resin was washed with DMF and dichloromethane and then, incubated with a mixture for cleavage (containing TFA: 1,2-ethanedithiol: triisopropyl silane: water at 92.5:2.5:2.5:2.5) at room temperature for 3 hours to deprotect the peptide and cleave it from the resin. Next, the peptide was precipitated in diethyl ether and pelletized by manual centrifugal treatment. The crudely formed peptide was dissolved in a water:acetonitrile (4:1) solution containing 0.1% TFA.

To macrocyclize the peptide, triethylamine was added to adjust the pH of the peptide solution to about 10. To complete macrocyclization of the peptide, the peptide solution was incubated at 42° C. for 1 hour.

The peptide was purified to a purity exceeding 95% by reverse phase HPLC (Cosmosil, 5C18-AR-300, 10×250 mm, Nacalai tesque) using a water and acetonitrile/0.1% TFA gradient. After removal of the acetonitrile from the peptide using a rotary evaporator, the residue was lyophilized. The peptide thus selected was dissolved in DMSO and the resulting solution was used as a stock solution. The stock peptide was diluted with water containing 50% (v/v) acetonitrile and the concentration was determined by a spectrophotometer. The purified peptide was lyophilized and dissolved in DMSO. The peptides thus synthesized were all analyzed using MALDI-TOF mass to confirm their molecular weight.

1-11. Cell Culture

HeLa cells were cultured in a minimum essential medium (MEM) supplemented with 10% (v/v) fetal bovine serum (FBS), penicillin (100 units/ml), and streptomycin (100 µg/ml) in a high-humidity incubator containing 5% CO2 (gas).

1-12. Confocal Microscope

HeLa cells proliferated on a 90-mm plate until they reached sub-confluence and Trypsin/EDTA were treated at 37° C. for one hour to release the cells from the plate. A culture dish (Iwaki) having a 35-mm glass bottom was seeded with $1\times10^4$ cells. They were cultured overnight in an MEM culture containing 10% FBS to attach the cells. The medium was removed and the cells were washed with an MEM medium containing 0.1% FBS.

The cells were incubated with 10 µM peptide (VB1C12-Flu, VB1C12-ana-Flu, VB1 C20-Flu, or VB1 C20-ana-Flu) and 1 ml of an MEM medium containing 3 µM DRAQ7 at 37° C. for 60 minutes. The latter ones were used for confirming cell integrity. The intracellular distribution of the fluorescently labeled peptide was analyzed using a Leica TCS SP2 microscope equipped with an N PLAN 40× objective lens, without washing and immobilization.

1-13. Colocalization Analysis

The HeLa cells proliferated and seeded as described above were incubated with 10 μM peptide (VB1C12-Flu, VB1C12-ana-Flu, VB1C20-Flu, or VB1 C20-ana-Flu) and 1 ml of an MEM medium containing 5 μM SYTO61 at 37° C. for 60 minutes.

The cells were analyzed as described above without washing and immobilization.

2. Results 2-1. In Vitro Selection of VB Peptide to be Bound to PAD4 by Using RaPID Display The in vitro selection of VB peptides to be bound to PAD4 peptide was performed using a RaPID system (FIG. 3). For selection of VB species having activity against PAD4, a VB1 mRNA library and a VB2 mRNA library were combined with the mRNA display method. First, each mRNA of the VB1 and VB2 mRNA libraries was bound to a puromycin-CC-(PEG linker)-DNA fragment to bind puromycin to the end of the mRNA. Next, the puromycin-bound mRNA library was translated using a FIT system having, instead of Met, $^{ClAc-D}$-F-tRNA$^{fMet}_{CAU}$ and Ahep-tRNA$^{Asn-E2}_{CAU}$. Supposing that 100 pm mRNA was used, the library of the first round was presumed to contain $1.7 \times 10^{13}$ or more kinds of peptides, a single copy per peptide.

In first round of the selection, the VB peptide library was mixed with PAD4 immobilized on His-Tag magnetic beads and a reverse transcription reaction and amplification of cDNA were performed before recovery. In the second round, prior to the selection of peptides to be bound to PAD4 immobilized beads, the library was treated only with magnetic Dynabeads (until 12 times), an undesired background-bound peptide was removed, and a peptide fraction not bound to the beads was provided for selection of peptides to be bound to PAD4 immobilized beads. Thus, a RaPID selection cycle was repeated to obtain a group of active peptides. As is expected, by repeating the PaPID selection cycle, in each of VB1 peptide library (FIG. 4A) and VB2 peptide (FIG. 4B) peptide library, active peptides are enriched in the 8th cycle.

2-2. Determination of Enriched Peptide Sequence

From 62 sequences, 11 peptide clones were identified (FIGS. 4C and 4D). Of these, 6 clones (FIG. 4C) were derived from the VB1 peptide library and 5 clones (FIG. 4D) were derived from the VB2 peptide library. Surprisingly, the peptide sequences were all hydrophobic and some sequences had, at the third position thereof, another cysteine, meaning that they were a lasso type cyclic peptide having the VB skeleton. All the clones having a determined sequence contained at least one Arg residue. PAD4 is known to convert peptidyl arginine into peptidyl citrulline by post-translational modification so that it has been suggested that this Arg reacts with an active site of PAD4. Therefore, these VB peptides are thought to be a candidate of a PAD4 inhibitor that specifically binds to PAD4.

2-3. Evaluation of PAD4 Inhibitory Effect of Selected VB Peptide

In order to study the binding affinity and physiological activity of the peptides thus obtained, VB1 peptides that had appeared with high frequency were prepared by Fmoc solid-phase synthesis without a linker sequence other than glycine. Binding affinity analysis performed using surface plasmon resonance (SPR) (FIGS. 5A and 5B) has revealed that VB1 peptides shows a high binding rate to PAD4 ($9.21 \times 10^4$-$1.21 \times 10^5$ M$^{-1}$s$^{-1}$) and a low dissociation rate ($3.56$-$6.64 \times 10^{-3}$ s$^{-1}$). As a result, it has been found that they have affinity as high as 38.7-54.9 nM (FIG. 5C).

2-4. In Vitro PAD4 Inhibition Assay

In vitro PAD4 inhibition assay was performed using colorimetric analysis (Jones, J. E., et al., 2012, ACS chemical biology, 7(1), 160-5) in order to study whether or not VB1C12 and VB1C20 could inhibit PAD4 activity. As a standard of PAD4 inhibitory activity, a recently discovered low-molecular compound inhibitor against PAD4 was used with the selected VB1 peptides. Correct $IC_{50}$ measurement was made, but according to the initial data (FIG. 6), VB1C12 and VB1C20 peptides both dose-dependently inhibit PAD4, but their inhibitory activity is not stronger than that of the existing PAD4 inhibitor.

2-5. Chemical modification for introducing a warhead (warhead) functional group into VB peptides In order to obtain VB peptides having improved inhibitory ability, VB peptides were chemically modified so as to change them into a warhead type PAD4 inhibitor. In this case, a haloacetamidine warhead was introduced into the VB1C12 peptide by modifying an Arg residue. Haloacetamidine-based inhibitors are known to have PAD inhibitory activity (Jones, 2012). These compounds covalently modify an active site cysteine (Cys645) inevitable for catalytic activity and irreversibly inactivate PAD4. Inactivation is thought to proceed by attacking the Cys645 thiolate on the iminium carbon of the haloacetamidine warhead and forms a tetrahedral intermediate. Next, His471 is thought to donate a proton to stabilize the intermediate and thereby promote halide displacement by the sulfur atom. The resulting three-membered sulfonium ring collapses to form a thioether adduct. As a result, the enzyme is inactivated.

Synthesis of VB1C12-Cl-amidine analog (described in experiment method) was performed using fmoc solid-phase peptide synthesis and coupling, on resin, of methyl 2-chloroacetimidate hydrochloride to N-α-benzoylornithine (Scheme 1). After the peptide was separated from the resin, the peptide was purified by reverse-phase HPLC. In order to study the PAD4 inhibitory ability of the VB1C12-Cl-amidine analog, the in vitro PAD4 inhibition assay was performed by the above-described colorimetric analysis. The chloroacetamidine warhead type VB peptide showed inhibitory ability by 2.7 times greater than that of the Cl-amidine and VB1C12 peptide (FIG. 7).

2-6. Intracellular Introduction Analysis of VB Peptide by Confocal Microscope

Hela cells were analyzed under a fluorescence microscopy to study transfer of the VB peptides to cytoplasm and nucleus. Fluorescently labeled VB peptides (VB1C12 and VB1C20) and analogs thereof having no VB skeleton were synthesized using standard fmoc solid-phase peptide synthesis. After purification through reverse phase HPLC, the resulting peptides were subjected to MLADI TOF analysis. The peptides used for this experiment are shown in FIG. 8.

The HeLa cells were incubated with the fluorescently labeled peptides, at 37° C. for 60 minutes. After washing, they were observed under a confocal fluorescence microscope. All the assays were performed using a small dish with a glass bottom so that not a sample having the cells mounted thereon but a sample in a buffer was observed. DRAQ7 (3 μM) is a far-red fluorescent dye and it dyes only the nuclei of permeable dead cells. When the peptides are incubated, this DRAQ7 is added to find whether the cells are alive or not.

When 1 μM of the VB1C12-Flu peptide and the HeLa cells were incubated, at 37° C. for 60 minutes, almost all the cells did not incorporate therein the peptide (FIG. 9). When 5 or 10 μM VB1C12-Flu peptide was used, on the other hand, some cells (from 5 to 10%) incorporated the peptide therein (FIG. 10). From the cells having the peptide incorporated therein, different patterns of enriched fluorescence were observed. From almost all the living HeLa cells, enriched fluorescence was observed in the nuclei (FIG. 11). On the other hand, when a fluorescently labeled peptide having no VB skeleton (VB1C12-ana-Flu) was used as a control, the peptide was not incorporated in the cells (FIG. 9) even if its amount was 10 µM, suggesting the importance of the VB skeleton. VB1C20-Flu, the other one of the fluorescently labeled VB peptides was incorporated in the cells at a relatively low incorporation ratio. In this case, at least 10 µM VB1C20 was necessary for incorporation of it in the HeLa cells (FIG. 10). The fluorescently labeled peptide (VB1C20-ana-Flu) used as a control was not incorporated at all in the cells, also suggesting the importance of the VB skeleton.

2-7. Colocalization of VB Peptide and SYTO61 Stain in Living HeLa Cells

The distribution of VB peptides incorporated in the HeLa cells was studied by double-labeling experiment (double-labeling experiment) of the fluorescently labeled VB peptides and SYTO61 (Molecular Probes). SYTO61 is a nucleic acid stain and it binds also to cytoplasm. FIG. 12 shows distribution of both VB1C12-Flu and VB1C20-Flu peptides and a merged image of the fluorescently labeled VB peptide and SYTO61 distributions. As can be observed from the HeLa cells treated with the VB peptides, the merged image shows that different patterns of fluorescence enrichment are localized in the nuclei.

The present inventors have built the hypothesis that the above phenomenon owes to high affinity of VB1C12 and VB1C20 peptides for PAD4 localized in the nuclei of cells. Localization of the VB1C12-Flu peptide in the HeLa cells has been elucidated in real time by obtaining a series of merged images of the HeLa cells treated with 10 µM VB1C12-Flu and 5 µM SYTO61 along a plurality of confocal planes (Z-direction) (FIG. 13). It has been confirmed from the series of Z-direction images that the VB1C12-Flu peptide forms a green fluorescent pattern in the nucleus.

2-8. Conclusion

VB peptide inhibitors against PAD4 were identified using the RaPID system. The VB peptides thus selected showed strong nanomolar level binding affinity for PAD4. These peptides showed dose-dependent inhibitory ability in in vitro inhibition assay of PAD4 but did not show stronger inhibitory activity than known PAD4 inhibitors.

Chemically synthesized Cl-amidine warhead analog of VB peptides however have improved inhibitory ability against PAD4. Intracellular incorporation of VB peptides has been confirmed as a result of researches on the permeability of VB peptides through HeLa cells.

What is claimed is:

1. A conformationally flexible macrocyclic peptide comprising a macrocyclic structure having 4 or more amino acids,
wherein at least two amino acids of the amino acids that constitute the macrocyclic structure are not adjacent to each other, are non-proteinogenic amino acids, and have a hydrophobic side chain each independently selected from the group consisting of: (i) substituted or unsubstituted, saturated or unsaturated, and linear or branched alkyl groups having 4, 5, or 6 carbon atoms, (ii) substituted or unsubstituted aryl groups, (iii) vinyl groups, (iv) polyoxypropylene groups, and (v) polysiloxane groups; and
the hydrophobic side chains interact with each other in the macrocyclic structure in a hydrophilic environment and are exposed on the exterior of the macrocyclic structure in a hydrophobic environment.

2. The macrocyclic peptide according to claim 1, wherein the macrocyclic structure of the macrocyclic peptide has from 5 amino acids to 20 amino acids, of which two are the amino acids having a hydrophobic side chain; and the amino acids having a hydrophobic side chain are arranged substantially opposite to each other in the macrocyclic structure.

3. The macrocyclic peptide according to claim 1, having cell membrane permeability.

4. A method of translationally synthesizing the macrocyclic peptide as claimed in claim 1, comprising:
a step of providing a nucleic acid that encodes the macrocyclic peptide, has codons encoding two amino acids necessary for the formation of a ring and codons encoding two amino acids having a hydrophobic side chain, and has, between two codons encoding the amino acids necessary for the formation of a ring, two codons encoding the amino acids having a hydrophobic side chain; and
a step of translating the nucleic amino acid in a cell-free translation system including tRNAs aminoacylated by the two amino acids necessary for the formation of a ring and the two amino acids having a hydrophobic side chain, respectively.

5. The method according to claim 4, wherein at least one of the tRNAs charged with the two amino acids necessary for the formation of a ring and the two amino acids having a hydrophobic side chain, respectively, is an artificial aminoacyl tRNA.

6. The method according to claim 4, wherein the two amino acids necessary for the formation of a ring are chloroacetylated amino acid and cysteine, respectively.

7. A screening method of the macrocyclic peptide as claimed in claim 1 having binding ability to a target molecule, comprising:
a step of forming a nucleic acid library including two or more nucleic acids including a nucleic acid that encodes the macrocyclic peptide, has codons encoding two amino acids necessary for the formation of a ring and codons encoding two amino acids having a hydrophobic side chain, has two codons encoding the amino acids having a hydrophobic side chain between two codons encoding the amino acids necessary for the formation of a ring, and includes a nucleic acid encoding a random amino acid sequence in a portion other than the codons encoding the amino acids necessary for the formation of a ring and the codons encoding the amino acids having a hydrophobic side chain;
a step of translating the nucleic acid library in a cell-free translation system to obtain a macrocyclic peptide library;
a step of bringing the macrocyclic peptide library into contact with a target molecule, followed by incubation; and
a step of selecting a macrocyclic peptide bound to the target molecule.

8. The nucleic acid library as claimed in claim 7.

9. The macrocyclic peptide library as claimed in claim 7.

10. A method of screening the macrocyclic peptide as claimed in claim 1 having binding ability to at target molecule, comprising:
- (a) a step of forming a library including two or more mRNAs including an mRNA encoding the macrocyclic peptide, having codons encoding two amino acids necessary for the formation of a ring and codons encoding two amino acids having a hydrophobic side chain, having two codons encoding the amino acids having a hydrophobic side chain between two codons encoding an amino acid necessary for the formation of a ring, and including an mRNA encoding a random amino acid sequence in a portion other than the codons encoding the amino acids necessary for the formation of a ring and the codons encoding the amino acids having a hydrophobic side chain;
- (b) a step of binding directly or indirectly puromycin to the 3' end of each of the mRNAs of the library;
- (c) a step of translating the nucleic acid of the library in a cell-free translation system to obtain an mRNA-macrocyclic peptide complex library;
- (d) a step of bringing the mRNA-macrocyclic peptide complex library into contact with the target molecule, followed by incubation;
- (e) selecting an mRNA-macrocyclic peptide complex group bound to the target molecule, obtaining a cDNA group by a reverse transcription reaction, and then amplifying the group; and
- (f) transcribing the cDNA group to obtain an mRNA library;

wherein the steps (a) to (f) are performed twice or more to enrich the macrocyclic peptide having binding ability to the target molecule.

* * * * *